(12) United States Patent
Li et al.

(10) Patent No.: US 8,501,762 B2
(45) Date of Patent: Aug. 6, 2013

(54) TETRAHYDROPROTOBERBERINE COMPOUNDS, THE SYNTHETIC METHOD AND THE USE THEREOF

(75) Inventors: Jianfeng Li, Shanghai (CN); Aixiang Liu, Shanghai (CN); Xinjian Chen, Shanghai (CN); Guozhang Jin, Shanghai (CN); Tiema Yan, Shanghai (CN); Rongxia Zhang, Shanghai (CN); Yi Zhu, Shanghai (CN); Yanjun Pan, Shanghai (CN); Jingshan Shen, Shanghai (CN); Jingkang Shen, Shanghai (CN)

(73) Assignees: Shanghai Institute of Materia Medica, Chinese Academy of Sciences, Shanghai (CN); Topharman Shanghai Co., Ltd., Shanghai (CN)

( * ) Notice: Subject to any disclaimer, the term of this patent is extended or adjusted under 35 U.S.C. 154(b) by 1121 days.

(21) Appl. No.: 11/988,441

(22) PCT Filed: Jul. 7, 2006

(86) PCT No.: PCT/CN2006/001601
§ 371 (c)(1),
(2), (4) Date: Feb. 11, 2009

(87) PCT Pub. No.: WO2007/006212
PCT Pub. Date: Jan. 18, 2007

(65) Prior Publication Data
US 2009/0149488 A1 Jun. 11, 2009

(30) Foreign Application Priority Data

Jul. 8, 2005 (CN) .......................... 2005 1 0027630

(51) Int. Cl.
*A61K 31/4353* (2006.01)
*C07D 221/18* (2006.01)
(52) U.S. Cl.
USPC .......................................... 514/284; 546/71
(58) Field of Classification Search
USPC .......................................... 514/284; 546/71
See application file for complete search history.

(56) References Cited

U.S. PATENT DOCUMENTS 3,932,384 A 1/1976 Sawa et al.

FOREIGN PATENT DOCUMENTS

CN 1603324 4/2005

OTHER PUBLICATIONS

Rajaraman, et al. Document No. 88:136828 (1977) retrieved from CAPLUS.*
Registry No. 58784-31-9; entered in STN on Nov. 16, 1984.*
Schaper. Document No. 132:44498 (1999) retrieved from CAPLUS.*
Yasukawa, et al. Document No. 115:247457 (1991) retrieved from CAPLUS.*
Jalander, et al. Document No. 114:3478 (1990) retrieved from CAPLUS.*
Bahadur, et al. Document No. 99:155239 (1983) retrieved from CAPLUS.*
O'Brien, et al. Document No. 91:20291 (1978) retrieved from CAPLUS.*
Hoshi, et al. Document No. 85:56540 (1976) retrieved from CAPLUS.*
Deulofeu, et al. Document No. 65:99511 (1966) retrieved from CAPLUS.*
Richter, et al. Document No. 82:171262 (1975) retrieved from CAPLUS.*
Sawa, et al. Document No. 80: 146050 (1974) retrieved from CAPLUS.*
Giacopello, et al. Document No. 67:64591 retrieved from CAPLUS.*
Barkovic, et al. Document No. 65:38663 (1966) retrieved from CAPLUS.*
Zhang, et al. Document No. 141:116418 (2003) retrieved from CAPLUS.*
Zhou, et al. Document No. 130:320855 (1996) retrieved from CAPLUS.*
Guo, et al. Document No. 127:44437 (1997) retrieved from CAPLUS.*
Tang, et al. Document 124:306521 (1996) retrieved from CAPLUS.*
Chen, et al. Document No. 124:278807 (1996) retrieved from CAPLUS.*
Iwasa, et al. Document No. 125:163064 (1996) retrieved from CAPLUS.*
Registry No. 47811-29-0; entered in STN on Nov. 16, 1984.*
Jin, et al. Document No. 133:83857 (2000) retrieved from CAPLUS.*
Knoll, Jozsef. Document No. 72:11208 (1968) retrieved from CAPLUS.*
Vippagunta, et al. Advanced Drug Delivery Reviews 48 (2001) 3-26.*
Schizophrenia [online] retrieved from CAPLUS. Feb. 7, 2010 (URL; http://www.ncbi.nlm.nih.gov/pubmedhealth/PMH0001925/).*

(Continued)

*Primary Examiner* — Shawquia Young
(74) *Attorney, Agent, or Firm* — Nixon & Vanderhye PC

(57) ABSTRACT

The present invention relates to tetrahydroprotoberberines of the formula (I) and the physiologically acceptable salts thereof. The invention also relates to the use of the compounds of the formula (I) or pharmaceutically acceptable salts thereof for preparing a pharmaceutical composition for the treatment of a medical disorder susceptible to treatment with dopamine receptor ligand, such as schizophrenia.

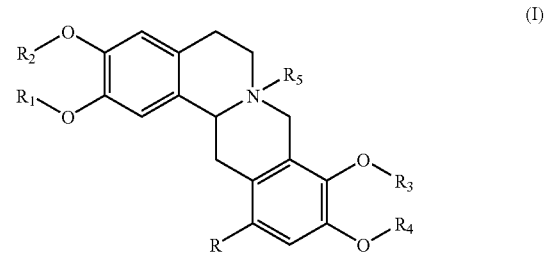

(I)

8 Claims, No Drawings

OTHER PUBLICATIONS

International Search Report for PCT/CN2006/001601 mailed Oct. 19, 2006.

Schaper, Klaus-Jurgen, "Free—Wilson-Type Analysis of Non-Additive Substituent Effects on THPB Dopamine Receptor Affinity Using Artificial Neural Networks", Quantitative Structure-Activity Relationships (1999), 18(4), pp. 354-360, 7 pages.

Guo et al., "Characteristics of tetrahydroprotoberberines on dopamine $D_1$ and $D_2$ receptors in calf striatum[1]", Zhongguo Yaoli Xuebao (1997), 18(3), pp. 225-230, 6 pages.

Chen et al., "Effect of (±) 12-chloroscoulerine on brain dopamine receptors", Zhongguo Yaoli Xuebao (1996), 17 (2), pp. 185-189, 5 pages.

Jalander et al., "Protoberberine Alkaloids From the Bark of *Enantia chlorantha*", Collect. Czech. Chem. Comm. (vol. 55) (1990), pp. 2095-2099, 5 pages.

Hanaoka et al., "Chemical Transformation of Protoberberines. Part 10.1 A Novel Synthesis of Sanguilutine and Dihydrosanguilutine, fully Aromatised 2, 3,7,8,10-Pentaoxygenated Benzo[c]phenanthridine Alkaloids", J. Chem. Soc. Perkin, (1987), pp. 677-681, 5 pages.

McMurtrey et al., "Kinetics and Product Distribution in Pictet-Spendler Cyclization of Tetrahydropapaveroline to Tetrahydroprotoberberine Alkaloids", Journal of Organic Chemistry (1984), 49(5), pp. 947-948, 2 pages.

Lin et al., "Structural elucidation and total synthesis of *Corydalis* L", Fudan Xuebao, Ziran Kexueban (1981), 20(4), pp. 446-449, 4 pages.

Pandey et al., "Synthesis of Heterocycles Via Lactones. Part III[1]. A Synthesis of berbines[2].—Synthesis of (±)-Scoulerine and Pseudorpitetrahydroberberine", Heterocycles, vol. 12, No. 10, (1979), pp. 1327-1330, 4 pages.

O'Brien et al., "Preferential Cleavage of the Methoxyl Grop Adjacent to a Phenolic Function in Polymethoxylated Isoquinolines", Heterocycles, vol. 11, (1978), pp. 347-350, 4 pages.

Chiang et al., "Synthesis of (±)-govadine", Chemical Abstract 91:5394 (1979), 1 page.

Sheppard et al., "The Dopamine-Sensitive Adenylate Cyclase of the Rat Caudate Nucleus-3. The Effect Fo Aporphines and Protoberberines", Biochemical Pharmacology, vol. 27, (1978), pp. 1113-1116, 4 pages.

Teitel et al., "Preferential Removal of a Methylenedioxy Group From Optically Active Isoquinolines", Heterocycles, vol. 5, 1976, pp. 85-90, 6 pages.

Kametani et al., "A Total Synthesis of (±)-Kikemanine", Journal of the Chemical Society, Section C, 1971, pp. 3318-3321, 4 pages.

Tani et al., "Studies on the Alkaloids of Fumariaceos Plants. X.[1)] Alkaloids of *Corydalis platycarpa* Makino. (1).", Yakugaku Zasshi, 1970, 90(3), pp. 407-411, 5 pages.

Sun et al., "Synthesis of Compounds Relatd to *Corydalis* B (Tetrahydropalmatine), Yaoxue Xuebao (1965), 12(5), pp. 314-318, 5 pages.

Tomita et al., "Studies on the Alkaloids of Menispermaceous Plants. CCVI, Alkaloids of Formosan *Stephania japonica* Miers. (3).", Yakugaku Zasshi (1964), 84(8), pp. 776-778, 3 pages".

Dong-Lu Bai et al.., "The Synthesis of Tetrahydropalmatine Analogues", Scientia Sinica, vol. XII, No. 2, 1963, pp. 191-199, 9 pages.

Tomita et al., "Reaction of Tetrahydropalmatine and Tetrahydrojatrorrhizine by Metallic Sodium in Liquid Ammonia", Yakugaku Zasshi (1959), 79, pp. 690-692, 3 pages.

Spath et al., "Alkaloids of Colombo root. V. A new base of Colombo root and the constitution of berberrubine and palmatrubine", Ber. (1926), 59B, pp. 1486-1496, 11 pages.

* cited by examiner

TETRAHYDROPROTOBERBERINE COMPOUNDS, THE SYNTHETIC METHOD AND THE USE THEREOF

This application is the U.S. national phase of International Application No. PCT/CN2006/001601 filed 7 Jul. 2006 which designated the U.S. and claims priority to Chinese Patent Application No. 200510027630.9 filed 8 Jul. 2005, the entire contents of each of which are hereby incorporated by reference.

TECHNICAL FIELD

The present invention relates to novel tetrahydroprotoberberines. The compounds possess valuable therapeutic properties and are suitable, especially, for treating diseases that respond to modulation of dopamine receptors, such as schizophrenia, parkinsonism, hyperactivity disorder or migraine et. al.

BACKGROUND ART

Recently, the pathogenesis of schizophrenia has been suggested to involve dysfunction of dopamine $D_1$ receptors in the medial prefrontal cortex (mPFC). Which is resulted in dopamine $D_2$ receptor hyperactivity in subcortical regions such as the ventral tegmental area (VTA) and the nucleus accumbens (NAc). $D_1$ receptors dysfunction is involved in the negative symptoms of schizophrenia whereas the $D_2$ receptors hyperactivity results in the positive symptoms of this disorder. According to this new hypothesis, an effective antipsychotic drug should have both $D_1$ receptor agonist and $D_2$ receptor antagonist dual actions.

Tetrahydroprotoberberine analogues (THPBs) have this dual actions, including l-Stepholidine (l-SPD) and l-chloroscoulerine (ZL94112235.2, CN03151464.2). l-SPD is an active ingredient of the Chinese herb *Stephania*. l-CSL is a derivative of l-SPD. In preliminary clinic studies, l-SPD showed favorable activity and few side effects in the treatment of schizophrenia. So, the efficacy of THPBs for neuron system disease especially schizophrenia merits further investigation.

DISCLOSURE OF THE INVENTION

The invention is based on the object of providing compounds of THPBs, as well as its pharmacologically acceptable salts and solvates, which act as highly affinity dopamine receptor ligands.

The present invention also relates to a preparation method of compounds of THPBs.

The present invention also relates to a method for treating disorder which respond to influencing by dopamine $D_1$ and $D_2$ receptor. And a method comprise administering an effective amount of at least one THPBs of the formula (I) and/or at least one physiologically acceptable salt of formula (I) to a subject in need thereof.

The present invention relates to the compounds of formula (I), pharmaceutically acceptable salts and solvates:

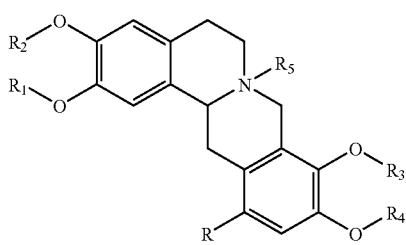

(I)

Wherein
R is H, halogen or cyano;
Each of $R_1$, $R_3$, $R_4$ is selected from H, $C_1$~$C_{12}$ alkyl, $(CH_2CH_2O)_nR_6$ (n=1~3), amino acid or N-protected amino acid, $COR_7$, $SO_2R_6$, $SO_2NR_9R_{10}$, or $R_1$ and $R_2$ together form $(CH_2)_n$, n is 1 or 2; when $R_1$, $R_3$, $R_4$ is $C_1$~$C_{12}$ alkyl, the alkyl is saturated or unsaturated alkyl, linear chain $C_1$~$C_{12}$ alkyl, branched chain $C_1$~$C_{12}$ alkyl, $C_1$~$C_{12}$ cycloalkyl, $C_1$~$C_{12}$ alkyl substituted by aryl, $COOR_6$ or $CONR_9R_{10}$; when $R_1$, $R_3$, $R_4$ is amino acid or N-protected amino acid, which is D-, L- or DL-amino acid or N-protected amino acid; the protecting groups is selected from Boc, Cbz or other protected group used in amino acid; $R_6$ is selected from H, $C_1$~$C_3$ alkyl or alkyl substituted by aryl; $R_7$ is selected from $C_1$~$C_{12}$ alkyl, alkyl substituted by $(CH_2CH_2O)_nR_6$ (n=1~3), alkoxy, $COR_8$, $(CH_2)_nNR_9R_{10}$, substituted aryl, unsubstituted aryl, heterocyclic radical selected from imidazolyl, pyrazolyl, pyrrolidinyl, pyridinyl; when $R_7$ is $C_1$~$C_{12}$ alkyl, the alkyl is saturated or unsaturated alkyl, linear chain $C_1$~$C_{12}$ alkyl, branched chain $C_1$~$C_{12}$ alkyl, $C_1$~$C_{12}$ cycloalkyl, $C_1$~$C_{12}$ alkyl substituted by carbonyl, phenyl, substituted phenyl or substituted aryl heterocyclic radical; $R_8$ is selected from H, alkyl, alkoxy or aryl; $R_9$ and $R_{10}$ is selected independently from H, $C_1$~$C_4$ alkyl substituted by $C_3$~$C_5$ cycloalkyl or $C_1$~$C_4$ alkoxy, or form heterocyclic radical selected from azacyclobutyl, pyrrolidinyl, piperidyl, piperazinyl or morpholinyl;
$R_2$ is selected from H, $C_1$~$C_3$ alkyl, or $R_1$ and $R_2$ together form $(CH_2)_n$, n is 1 or 2;
$R_5$ is H, O, $C_1$~$C_3$ alkyl, substituted $C_1$~$C_3$ alkyl, halogen or aryl, or there is not $R_5$.

In the definition mentioned above, halogen is F, Cl, Br or I; any two of $R_1$, $R_2$, $R_3$, $R_4$ are same or different group mentioned above.

In particular, when R is H, $R_1$~$R_4$ is limited as follow:
When $R_1$ is H and $R_2$=$R_3$=$CH_3$, $R_4$ is unsubstituted $C_2$~$C_{12}$ alkyl, substituted $C_2$~$C_{12}$ alkyl, $(CH_2CH_2O)_nR_6$ (n=1~3), amino acid or N-protected amino acid, $COR_7$, $SO_2R_6$ or $SO_2NR_9R_{10}$.
When $R_1$ is H and $R_2$=$R_4$=$CH_3$, $R_3$ is unsubstituted $C_2$~$C_{12}$ alkyl, substituted $C_2$~$C_{12}$ alkyl, $(CH_2CH_2O)_nR_6$ (n=1~3), amino acid or N-protected amino acid, $COR_7$, $SO_2R_6$ or $SO_2NR_9R_{10}$.
When $R_1$ is $CH_3$, $R_2$ is $CH_3$, and one of $R_3$ and $R_4$ is unsubstituted $C_2$~$C_{12}$ alkyl, substituted $C_2$~$C_{12}$ alkyl, $(CH_2CH_2O)_nR_6$(n=1~3), amino acid or N-protected amino acid, $COR_7$, $SO_2R_6$ or $SO_2NR_9R_{10}$.
When $R_1$ is $CH_2Ph$, one of $R_3$ and $R_4$ is unsubstituted $C_2$~$C_{12}$ alkyl, substituted $C_2$~$C_{12}$ alkyl, $(CH_2CH_2O)_nR_6$ (n=1~3), amino acid or N-protected amino acid, $COR_7$, $SO_2R_6$ or $SO_2NR_9R_{10}$.
When $R_1$ and $R_2$ together form $CH_2$, $R_3$ or $R_4$ can't be selected from H, $CH_3$, $C_2H_5$ or $COCH_3$ at the same time.
When R is halogen, the compounds described in this invention exclude followed known compounds:
2,9-dihydroxy-3,10-dimethoxy-12-chloro-5,8,13,13a-tetrahydro-6H-dibenzo[a,g]quinolizine;
2,10-dihydroxy-3,9-dimethoxy-12-chloro-5,8,13,13a-tetrahydro-6H-dibenzo[a,g]quinolizine;
2,3,9,10-tetramethoxy-12-chloro-5,8,13,13a-tetrahydro-6H-dibenzo[a,g]quinolizine;
2,9-dihydroxy-3,10-dimethoxy-12-bromo-5,8,13,13a-tetrahydro-6H-dibenzo[a,g]quinolizine;
2,10-dihydroxy-3,9-dimethoxy-12-bromo-5,8,13,13a-tetrahydro-6H-dibenzo[a,g]quinolizine;
3,9-dihydroxy-2,10-dimethoxy-12-bromo-5,8,13,13a-tetrahydro-6H-dibenzo[a,g]quinolizine;

9,10-dihydroxy-2,3-dimethoxy-12-bromo-5,8,13,13a-tetrahydro-6H-dibenzo[a,g]quinolizine;
2,3,9,10-tetramethoxy-12-bromo-5,8,13,13a-tetrahydro-6H-dibenzo[a,g]quinolizine;
2,9-dihydroxy-3,10-dimethoxy-12-fluoro-5,8,13,13a-tetrahydro-6H-dibenzo[a,g]quinolizine;
2,9-dihydroxy-3,10-dimethoxy-12-iodo-5,8,13,13a-tetrahydro-6H-dibenzo[a,g]quinolizine;
2,3-methylenedioxyl-9-hydroxy-10-methoxy-12-chloro-5,8,13,13a-tetrahydro-6H-dibenzo[a,g]quinolizine;
2,3-methylenedioxyl-9-hydroxy-10-methoxy-12-bromo-5,8,13,13a-tetrahydro-6H-dibenzo[a,g]quinolizine.

Formula (I) has one or several chiral carbons. So the chiral isomers exist, including enantiomers, unenantiomers or its mixture. This invention including the R—, and S— enantiomers and its mixture. The enantiomer can be separated by optical resolution with chemical method or separated by chiral HPLC. It also can be obtained by asymmetry synthesis.

The present invention relates to radioactivity derivatives of formula (I), which is suitable for biological studies.

The present invention also relates to the physiologically acceptable acid addition salts and alkali derivatives of formula (I). The acid addition salts are salts of the compounds of formula (I) with acid, including hydrochloric acid, hydrobromic acid, sulfuric acid, phosphoric acid, carbonic acid, organic sulfonic acid. The alkali derivatives is salts obtained by reacting the compounds of formula (I) with alkali, especially alkali metal derivatives, including natrium or potassium derivatives.

In the preferred embodiments of the compounds of formula (I), $R_1$ is H, $COR_7$, amino acid, or $R_1$ and $R_2$ together forms $CH_2$; $R_7$ is selected from $C_1~C_{12}$ alkyl, $COR_8$, alkoxy, or alkyl substituted by $(CH_2CH_2O)_nR_6$ (n=1~3); $R_6$ is H, $C_1~C_3$ alkyl or alkyl substituted by aryl; $R_8$ is alkoxy; $R_2$ is H, methyl, or $R_2$ and $R_1$ together form $CH_2$; $R_3$ is H, $COR_7$ or amino acid; $R_4$ is H, methyl or amino acid; R is H, Cl or F.

The following compounds of formula (I) are particularly preferred:
2-hydroxy-3,10-dimethoxy-9-acetoxy-12-chloro-5,8,13,13a-tetrahydro-6H-dibenzo[a,g]quinolizine;
2,9-diacetoxy-3,10-dimethoxy-12-chloro-5,8,13,13a-tetrahydro-6H-dibenzo[a,g]quinolizine;
2-hydroxy-3,10-dimethoxy-9-(2-hydroxy-ethoxy)-12-chloro-5,8,13,13a-tetrahydro-6H-dibenzo[a,g]quinolizine;
2-hydroxy-3,10-dimethoxy-9-ethoxycarbonyloxy-12-chloro-5,8,13,13a-tetrahydro-6H-dibenzo[a,g]quinolizine;
2-benzyloxy-3,10-dimethoxy-9-phenylalanyloxy-12-chloro-5,8,13,13a-tetrahydro-6H-dibenzo[a,g]quinolizine;
2,9-diacetoxy-3,10-dimethoxy-5,8,13,13a-tetrahydro-6H-dibenzo[a,g]quinolizine;
2,9-bis-{2-[2-(2-methoxy-ethoxy)-ethoxy]-acetoxy}-3,10-dimethoxy-12-chloro-5,8,13,13a-tetrahydro-6H-dibenzo[a,g]quinolizine;
2-hydroxy-3,10-dimethoxy-9-{2-[2-(2-methoxy-ethoxy)-ethoxy]-acetoxy}-12-chloro-5,8,13,13a-tetrahydro-6H-dibenzo[a,g]quinolizine;
2,3,9,10-tetrahydroxy-12-chloro-5,8,13,13a-tetrahydro-6H-dibenzo[a,g]quinolizine;
(−)-2,9-diacetoxy-3,10-dimethoxy-12-chloro-5,8,13,13a-tetrahydro-6H-dibenzo[a,g]quinolizine;
(−)-2,10-diacetoxy-3,9-dimethoxy-5,8,13,13a-tetrahydro-6H-dibenzo[a,g]quinolizine;
(−)-2-hydroxy-3,10-dimethoxy-9-acetoxy-12-chloro-5,8,13,13a-tetrahydro-6H-dibenzo[a,g]quinolizine;
2,3-methylenedioxyl-9,10-dimethoxy-12-fluoro-5,8,13,13a-tetrahydro-6H-dibenzo[a,g]quinolizine.

The present invention also related to the method of preparing the compounds of formula (I) and its derivatives.

The compounds of the formula (I) can be prepared by analogy to methods which are well known in the literatures. A preferred method for the preparation of compounds (I) is outlined below:
1. Preparation from Formula (II):

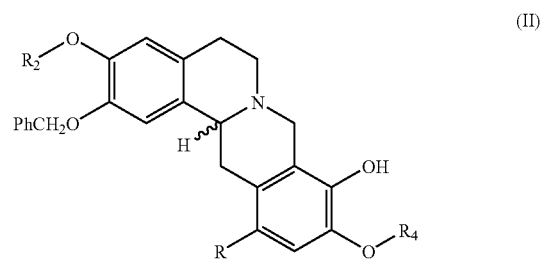

(II)

Compound of formula (II) is reacted with compound of formula (III) to prepare compound of formula (I):

$R_3Y$ (III)

Wherein $R_3$ is defined as described above, Y is halogen or hydroxy.

(1) Compound of formula (II) is reacted with $R_3Cl$ or $R_3Br$. The temperature is in the range of 0° C.-100° C. The reaction is catalysted by appropriate alkali. In detail, in the present of inorganic alkali (for example: NaOH, KOH, CsOH, Ba(OH)$_2$, Mg(OH)$_2$, Ca(OH)$_2$, KHCO$_3$, K$_2$CO$_3$, Na$_2$CO$_3$, Cs$_2$CO$_3$) or organic alkali (for example: sodium alkoxide, NEt$_3$, N(C$_4$H$_9$)$_3$, N(C$_3$H$_7$)$_3$, et al), the mixture was stirred at 0-100° C. for 2-24 hours to give compound of formula (I). The solvent can be selected in alcohol (for example: methanol, ethanol, isopropanol, C$_4$H$_9$OH, iso-C$_4$H$_9$OH, t-C$_4$H$_9$OH, C$_5$H$_{11}$OH, iso-C$_5$H$_{11}$OH), the mixture solution of alcohol and water (alcohol:water=5:9.5-9.5:0.5, V:V) or other solvent (for example: DMF, CH$_2$Cl$_2$, DMSO, THF, dioxane, pyrrolidinylone, acetone and CH$_3$OCH$_2$CH$_2$OCH$_3$).

(2) Compound of formula (II) is treated with $R_3COCl$, $R_3CO)_2O$ or $R_3CO)_2O$. The reaction carry through in the present of appropriate alkali at 0-100° C. In detail, in the present of inorganic alkali (for example: NaOH, KOH, CsOH, Ba(OH)$_2$, Mg(OH)$_2$, Ca(OH)$_2$, KHCO$_3$, K$_2$CO$_3$, Na$_2$CO$_3$, Cs$_2$CO$_3$) or organic alkali (for example: pyridine, NEt$_3$, N(C$_4$H$_9$)$_3$, N(C$_3$H$_7$)$_3$, et al), the mixture was stirred at 0-100° C. for 2-8 hours to give compound of formula (I). The solvent can be selected in pyridine, DMF, CH$_2$Cl$_2$, DMSO, THF, dioxane and pyrrolidone derivatives. The catalyst such as DMAP is added according the reaction conditions.

(3) Compound of formula (II) is reacted with ClSO$_2$R$_6$, or ClSO$_2$NR$_9$R$_{10}$. The reaction carry through in the present of appropriate alkali at 0° C. to room temperature. In detail, in the present of inorganic alkali (for example: NaOH, KOH, CsOH, Ba(OH)$_2$, Mg(OH)$_2$, Ca(OH)$_2$, KHCO$_3$, K$_2$CO$_3$, Na$_2$CO$_3$, Cs$_2$CO$_3$) or organic alkali (for example: pyridine, NEt$_3$, N(C$_4$H$_9$)$_3$, N(C$_3$H$_7$)$_3$, et al), the mixture was stirred at 0-100° C. for 2-8 hours to give compound of formula (I). The solvent can be selected in pyridine, DMF, CH$_2$Cl$_2$, DMSO, THF, dioxane and pyrrolidone derivatives.

(4) Compound of formula (II) is reacted with N-protected amino acid. The reaction of THPBs with amino acid can be finished through the procedure of esterification. For example, starting from the chloroacetyl derivatives of amino acid to give the desired compound. Another method is treat THPBs and amino acid in the present amino acid catalyst. In detail, the reaction is carried through at 0° C. to room temperature to give compound of formula (I). The solvent can be selected in $CH_2Cl_2$, DMF or THF. The catalyst can be selected in DCC, CDI, EDCI or other coupled reagent, accompanied by HOBt or DMAP.

(5) The deprotection of N-deprotected amino acid derivatives of THPBs (II) is carried through in the present of acid. In detail, the reaction is carried through at 0° C. to room temperature in the present of inorganic acid (for example: HCl, $H_2SO_4$, et al) or organic acid (for example: toluenesulfonic acid, $CF_3COOH$, AcOH, et al). The solvent can be selected in $CH_2Cl_2$, THF, et al.

(6) When $R_1$=H, compound of formula (I) was obtained by hydrogenating the compound of formula (II) ($R_1$=$CH_2Ph$) in the present of catalyst in order to avoid the hydrogenate of halogen in THPBs. In detail, compound of formula (II) is hydrogenated in the present of Raney-Ni at 0-40° C. for 1-10 hours to give compound of formula (I). The solvent is alcohol (for example: methanol, ethanol, isopropanol, et al) or the mixture solution of alcohol and water.

Compound of formula (II) is given as follow:

A) When $R_2$=$R_4$=$CH_3$ and R=Cl, that is 2-benzyloxy-3,10-dimethoxy-9-hydroxy-12-chloro-5,8,13,13a-tetrahydro-6H-dibenzo[a,g]quinolizine (compound IIA). Intermediate IIA is preparation according to the method reported in literature (CN03151464.2), and (−)-IIA is obtained through resolution from IIA (CN03151464.2).

B) When $R_2$, $R_4$ is other substituted groups, the hydroxyl derivatives of THPBs can be obtained by debenzyloxy or demethyl reaction of compound of formula (II) ($R_2$=$R_4$=$CH_3$) in the present of $BBr_3$. This compound is esterificated, etherificated, coupled with amino acid or demethylatied to provide the compound of formula (II). The procedure is described above.

2. Preparation from Formula (IV):

(IV)

R is Cl, H.

Compound of formula (IV) is treated with compound of formula (III) to preparation formula (I):

$R_1Y$ (or $R_3Y$)　　　(III)

Wherein $R_1$ (or $R_3$) is definited as described above, Y is halogen or hydroxy.

(1) Compound of formula (IV) is react with $R_1Cl$ or $R_1Br$. The procedure is the same as the synthetic procedure described in the reaction of compound of formula (II) with $R_3Cl$ or $R_3Br$. The structure of compound of formula (I) is different according the amount of compound of formula (III) and the activity of the hydroxy of compound of formula (IV).

(2) Compound of formula (IV) is reacted with $R_1COCl$, $(R_1CO)_2O$ or $(R_3CO)_2O$. The procedure is the same as the synthetic procedure described in the reaction of compound of formula (II) with $R_1COCl$, $(R_1CO)_2O$ or $(R_3CO)_2O$. The structure of compound of formula (I) is different according the amount of compound of formula (III) and the activity of the hydroxy of compound of formula (IV).

Compound of formula (IV) is given as follow:

(1) When R is Cl, compound of formula (IV) is given as follow:

Compound of formula (II) ($R_2$=$R_4$=$CH_3$, R=Cl) was debenzylization with common method to give compound of formula (VI) (R=Cl). The methods are hydrogenate or hydrolysis by acid. In detail, compound of formula (II) is hydrogenated in the present of Raney-Ni at 0~40° C. for 1~10 hours to give compound of formula (VI) (R=Cl). The solvent is alcohol (for example: methanol, ethanol, isopropanol, et al) or the mixture solution of alcohol and water. Alternatively, compound of formula (II) is heat with acid (for example: HCl, $H_2SO_4$, HBr, et al) to debenzylate. The solvent is acid (HCOOH, AcOH, et al) or alcohol (such as ethanol).

(2) When R is H, compound of formula (IV) is given as follow:

Compound of formula (II) ($R_2$=$R_4$=$CH_3$, R=Cl) is hydrogenated in the present of Pd—C under high pressure to give formula (IV) (R=H). In detail, compound of formula (II) is hydrogenated at 20-60° C. for 3~24 hours in the present of acid (for example: HCl/$H_2O$, $H_2SO_4$/$H_2O$, HBr/$H_2O$, et al) to give compound of formula (IV) (R=H). The solvent is alcohol (for example: methanol, ethanol, isopropanol, et al) or other solvent (DMF, DMSO, THF, et al).

3. Preparation from Formula (V):

(V)

Compound of formula (V) is natural product l-SPD, isolated from plants. Staring from l-SPD, the compound of formula (I) can be provided by esterification, etherification, coupling with amino acid or demethylation. The procedure is described above.

4. The Preparation of N-Substituted Derivatives of Formula (I)

The free base of compound of formula (I) is reacted with alkyl halide (for example; $CH_3I$) or substituted halide alkyl (for example; $PhCH_2Br$) at room temperature to 100° C., followed by precipitating when cooling, or by separating through column chromatography to give the target product;

5. Preparation from Formula (VI):

(VI)

Compound of formula (VI) was reacted with $HNO_2$ to give diazo salts, which is react with corresponding reagent to give the compound of formula (I) (R=halogen, cyano).

Compound of formula (VI) can be prepared as follow:

Nitration of compound of formula (I) (R=H) to give nitro derivatives, which is reduced to give compound of formula (VI). The nitro derivatives of compound of formula (I) also can be obtained by cyclization of nitro benzylisoqunoline derivatives.

The physiologically acceptable acid addition salts of formula (I) can be obtained by the conventional methods in the literature. For example, the compound of formula (I) was treated with appropriate acid in appropriate solvent, and the salt can be obtained through evaporating solvents or filtrating.

The compound of formula (I) was treated with appropriate alkali to give physiologically acceptable alkali addition salts.

The pharmacological actions of the compound according to the present invention are detected through the following methods.

1. Dopamine Receptor Binding Studies

The affinities of these compounds on dopamine receptors were evaluated with competitive receptor binding assays (Acta Pharmacol Sin, 1989, 10:104 and Acta Pharmacol Sin, 2003, 24(3): 225-229). The Ki is calculated according the inhibition data tested.

l-CSLMS is S-chloroscoulerine mesylate and CSL is chloroscoulerine.

TABLE 1

Affinities of THPBs for binding to dopamine receptors[a]

| Example | Inhibition(%) for $D_1$ | Inhibition(%) for $D_2$ |
|---|---|---|
| 7 | 100 | 100.0 |
| 8 | 100.0 | 93.8 |
| 17 | 97.9 | 57.4 |
| 21 | 100.0 | 100.0 |
| 23 | 77.5 | 44.0 |
| 34 | 99.4 | 90.7 |
| 42 | 96.2 | 39.7 |
| 44 | 100.0 | 93.3 |
| 47 | 100.0 | 77.4 |
| 50 | 100.0 | 58.5 |
| 63 | 95.2 | — |

[a]Inhibition(%) data was tested at $1 \times 10^{-5}$ mol/L

TABLE 2

Ki values of THPBs for bingding to dopamine receptors

| | Ki | |
|---|---|---|
| Example | $D_1$(nM) | $D_2$(μM) |
| l-CSLMS | — | 1.7 ± 0.5 |
| CSL | 6.1 ± 3.0 | — |
| 7 | 10.7 ± 1.0 | 6.9 ± 1.5 |
| 21 | 2.6 ± 0.7 | — |
| 34 | 51.8 ± 32.2 | 10.6 ± 2.6 |
| 42 | 35.4 ± 4.4 | 14.9 ± 0.2 |
| 43 | 403.5 ± 188.3 | — |

2. 6-OHDA-Lesioned Rats Rotation Test

Some of the compounds were evaluated on 6-OHDA-lesioned rats model. In this model, compounds of example 7, 44 and 48 exhibit positive effects at 10 mg/kg.

3. PCP-Induced Immobility Test in Mice

Phencyclidine(PCP)-induced immobility test in mice was selected as the model to evaluate the antipsychotic effect of some compounds of the present invention (Br J Pharmacol, 1995, 116: 2531-2537). The dose is selected according the $ED_{50}$ of l-CSLMS. Given PCP, immobility times of mice was increased, whereas the active compound can decrease the immobility time. At 20 mg/kg (i.g.), the immobility time of compound of example 47 is 54.9±19 s, and the immobility time of l-CSLMS is 48.0±27 s, which has statistically significant differences (P<0.05) compared to PCP group (78.1±28 s).

The present invention therefore relates to compounds of formula (I) and physiologically acceptable salts.

The present invention therefore relates to a pharmaceutical composition which comprises at least one compound of the formula (I) and/or at least one physiologically acceptable addition salt of (I), together with physiologically acceptable carriers and/or auxiliary substances.

The present invention also relates to a method for treating disorder which respond to influencing by dopamine $D_1$ and $D_2$ receptor. And a method comprise administering an effective amount of at least one THPBs of the formula (I) and/or at least one physiologically acceptable addition salt of (I) to a subject in need thereof.

The present invention also relates to all the new intermediates described in this invention.

THE PREFERABLE EMBODIMENTS OF THE INVENTION

The following examples serve to explain the invention without limiting it.

The compounds were characterized either via $^1$H NMR or MS.

The compound in formula (II), when $R_2=R_4=CH_3$, R=Cl, i.e. the intermediate 2-benzyloxy-3,10-dimethoxy-9-hydroxy-12-chloro-5,8,13,13a-tetrahydro-6H-dibenzo[a,g]quinolizine (compound IIA), which is prepared according to the method reported in literature (CN03151464.2), (−)-IIA is obtained through the resolution from IIA (CN03151464.2).

Preparation 1

2-benzyloxy-3,10-dimethoxy-9-hydroxy-12-chloro-5,8,13,13a-tetrahydro-6H-dibenzo[a,g]quinolizine (compound IIA)

1-(2'-chloro-4'-methoxy-5'-hydroxy)benzyl-6-methoxy-7-benzyloxy-1,2,3,4-tetrohydroisoquinolin (compound of formula VII) (103 g, 0.235 mol) was added methanol (5150 ml) and hydrochloric acid to adjust pH1-2. The mixture was then added 37% HCHO (3090 ml) and water (2000 ml). After stirring for 2 days, the solvent was evaporated and the residue was neutralized with $NaHCO_3$ to pH 9. The aqueous was extract with $CHCl_3$. The combined organic layers was dried and concentrated to give desired compound (103 g, 97.3%).

Example 1

2,9-dihydroxy-3,10-dimethoxy-12-chloro-5,8,13,13a-tetrahydro-6H-dibenzo[a,g]quinolizine Compound IIA (1.0 g, 2.2 mmol) was dissolved in $CH_3OH$, and Raney-Ni was added. The mixture was stirred for 2-5 hours under hydrogen at normal pressure and room temperature. After filtering the catalyst, the filtrate was concentrated to give the product as pink powder (0.73 g, 90.8%). That is chloroscoulerine. mp 136~138° C. $^1$HNMR ($CDCl_3$) δ: 2.57~2.70 (3H, m, $CH_2$), 3.09~3.22 (2H, m, $CH_2$), 3.21~3.39 (1H, dd, $CH_2$), 3.45~3.54 (5H, m, $CH_2$, N—CH and $CH_3OH$), 3.85 (3H, s, Ar—$OCH_3$), 3.88 (3H, s, Ar—$OCH_3$), 4.20 (1H, d, $CH_2$), 5.50 (1H, brs, OH), 5.63 (1H, brs, OH), 6.60 (1H, s, ArH), 6.80 (1H, s, ArH), 6.89 (1H, s, ArH).

Example 2

2,9-dihydroxy-3,10-dimethoxy-5,8,13,13a-tetrahydro-6H-dibenzo[a,g]quinolizine hydrochloride Compound IIA (2.0 g, 4.4 mmol) was dissolved in $CH_3OH$ (200 ml), adding 1 mol/L hydrochloric acid (5 ml) and 10% Pd—C (0.3 g). The mixture was hydrogenated under pressure at 50-60° C. for 12 hours. After the raw material disappeared detected with TLC, filtering the catalyst, the filtrate was concentrated to give the product as beige powder (1.5 g, 93%). That is scoulerine, which can be used as a intermediate for next step. mp 246° C. $^1$HNMR (DMSO-$d_6$) δ: 2.46~2.60 (3H, m, $CH_2$), 3.13 (1H, m, $CH_2$), 3.14~3.30 (4H, m, $CH_2$ or N—CH), 3.74 (3H, s, Ar—$OCH_3$), 3.76 (3H, s, Ar—$OCH_3$), 4.03 (1H, d, $CH_2$), 6.59 (1H, d, ArH), 6.64 (1H, s, ArH), 6.70 (1H, s, ArH), 6.78 (1H, d, ArH).

Example 3

2-benzyloxy-3,10-dimethoxy-9-benzoyloxy-12-chloro-5,8,13,13a-tetrahydro-6H-dibenzo[a,g]quinolizine Compound IIA (0.5 g, 1.1 mmol) was dissolved in $CH_2Cl_2$ (30 ml), adding benzoyl chloride (0.2 g, 0.17 ml, 1.4 mmol) and triethylamine (0.19 ml). The mixture was stirred at room temperature for 5 hours. After the raw material disappeared detected with TLC, the mixture was poured into water, adding 1 mol/L NaOH. The aqueous phase was extracted three times with $CH_2Cl_2$. The combined organic phase were washed with brine and dried over $Na_2SO_4$, filtered, and the solvent was evaporated under reduced pressure. The residue was purified by silica chromatography (ethyl acetate/petroleum ether=1/5) and recrystallized with ethyl acetate/petroleum ether to give the product as pale yellow powder. mp 170-172° C.

Example 4

2-hydroxy-3,10-dimethoxy-9-benzoyloxy-12-chloro-5,8,13,13a-tetrahydro-6H-dibenzo[a,g]quinolizine A product obtained in Example 3 (0.183 g, 0.33 mmol) was add $CH_3OH$ (15 ml) and Raney-Ni. The mixture was hydrogenated at room temperature for 1 hours. The mixture was filtered, and the filtrate was concentrated to give the product as yellow-green solide (0.16 g). The solide was recrystallized with ethyl acetate/petroleum ether to give pale yellow powder (0.041 g, 26.7%). mp 162~164° C. $^1$HNMR (CDCl$_3$) δ: 2.57~2.71 (3H, m, $CH_2$), 3.08~3.12 (2H, m, $CH_2$), 3.36~3.58 (3H, m, $CH_2$ and N—CH), 3.79 (3H, s, Ar—$OCH_3$), 3.87 (3H, s, Ar—$OCH_3$), 4.02 (1H, br, $CH_2$), 5.55 (1H, s, Ar—OH), 6.59 (1H, s, ArH), 6.89 (1H, s, ArH), 6.95 (1H, s, ArH), 7.51~7.56 (2H, m, PhH), 7.65~7.67 (1H, m, PhH), 8.22~8.24 (2H, m, PhH). MS (EI) m/z: 464 (M−1), 360, 344, 178, 105 (base), 77.

Example 5

2,9-dibenzoyloxy-3,10-dimethoxy-12-chloro-5,8,13,13a-tetrahydro-6H-dibenzo[a,g]quinolizine A product obtained in Example 1 (0.15 g, 0.41 mmol) was suspend on $CH_2Cl_2$ (20 ml), adding benzoyl chloride (0.22 ml) and triethylamine (0.26 ml). The mixture was stirred at room temperature for 7 hours. Then the reaction was diluted with $CH_2Cl_2$ (10 ml), followed by adding 0.5 mol/L n NaOH. The aqueous phase was extracted two times with $CH_2Cl_2$. The combined organic layers were washed with water, brine and dried over $Na_2SO_4$, filtered, and the solvent was evaporated under reduced pressure. The residue was purified by silica chromatography (ethyl acetate/petroleum ether=1/4) to give pale yellow powder (0.18 g, 76.2%). The analytic sample was recrystallized by ethyl acetate/petroleum ether. mp 152~154° C. $^1$HNMR (CDCl$_3$) δ: 2.61~2.76 (3H, m, $CH_2$), 3.14 (2H, m, $CH_2$), 3.36~3.41 (2H, m, $CH_2$ and N—CH), 3.61 (1H, m, $CH_2$), 3.78 (3H, s, Ar—$OCH_3$), 3.80 (3H, s, Ar—$OCH_3$), 4.09 (1H, br, $CH_2$), 6.75 (1H, s, ArH), 6.95 (1H, s, ArH), 7.11 (1H, s, ArH), 7.50~7.56 (4H, m, PhH), 7.62~7.67 (2H, m, PhH), 8.23~8.25 (4H, m, PhH).

Example 6

2-benzyloxy-3,10-dimethoxy-9-acetoxy-12-chloro-5,8,13,13a-tetrahydro-6H-dibenzo[a,g]quinolizine Compound IIA (0.5 g, 1.1 ml) was dissolved in pyridine (10 ml), adding acetyl anhydride (1 ml). The mixture was stirred at room temperature for 2 hours. Then the mixture was concentrated to small volume and poured into water, adjusting to pH 8 with saturated $NaHCO_3$. The aqueous phase was extracted three times with $CH_2Cl_2$. The combined organic layers were washed with water, brine and dried over $Na_2SO_4$, filtered, and the solvent was evaporated under reduced pressure. The residue was discolored by activated carbon and recrystallized with $CH_2Cl_2$/hexane to give product (0.246 g, 45%). mp 150~152° C. $^1$HNMR (CDCl$_3$) δ: 2.33 (3H, s, $COCH_3$), 2.49~2.71 (3H, m, $CH_2$), 3.12~3.15 (3H, m, $CH_2$), 3.39~3.52 (2H, m, $CH_2$ and N—CH), 3.80 (3H, s, Ar—$OCH_3$), 3.88 (3H, s, Ar—$OCH_3$), 3.98 (1H, d, $CH_2$), 5.16 (2H, q, Ph-$CH_2$), 6.63 (1H, s, ArH), 6.76 (1H, s, ArH), 6.90 (1H, s, ArH), 7.26~7.32 (1H, m, PhH), 7.35~7.39 (2H, t, PhH), 7.45~7.47 (2H, d, PhH).

Example 7

2-hydroxy-3,10-dimethoxy-9-acetoxy-12-chloro-5,8,13,13a-tetrahydro-6H-dibenzo[a,g]quinolizine A product obtained in Example 6 (0.070 g, 0.114 mmol) was add $CH_3OH$ (15 ml) and Raney-Ni. The mixture was hydrogenated at room temperature for 2 hours. The mixture was filtered, and the filtrate was concentrated to give the product as pale yellow oil. The oil was recrystallized with ethyl acetate/petroleum ether (1/3) to give pale yellow powder (0.022 g, 38.4%). mp 191~192° C. Anal: Cacul: C, 62.45%; H, 5.49%; N, 3.47%; test: C, 62.19%; H, 5.41%; N, 3.22%. $^1$HNMR (CDCl$_3$) δ: 2.34 (3H, s, $COCH_3$), 2.58~2.69 (3H, m, $CH_2$), 3.10~3.15 (2H, m, $CH_2$), 3.33~3.43 (2H, m, $CH_2$ and N—CH), 3.52~3.56 (1H, brd, $CH_2$), 3.80 (3H, s, Ar—$OCH_3$), 3.88 (3H, s, Ar—$OCH_3$), 3.99 (1H, d, $CH_2$), 5.54 (1H, s, Ar—OH), 6.59 (1H, s, ArH), 6.87 (1H, s, ArH), 6.91 (1H, s, ArH). MS (EI) m/z: 405 (M+2), 403 (M$^+$), 360, 344 (基峰), 186, 149, 91.

Example 8

2,9-diacetoxy-3,10-dimethoxy-12-chloro-5,8,13,13a-tetrahydro-6H-dibenzo[a,g]quinolizine acetate A product obtained in Example 1 (0.2 g, 0.55 mmol) was dissolved in pyridine (10 ml), adding acetyl anhydride (1 ml).

The mixture was stirred at room temperature overnight. The mixture was concentrated to small volume under reduced pressure. The solution was adding water (5 ml) slowly with stirring. The solid precipitated was collected by filtration and dryed at 50° C. to give gray powder (0.151 g, 61.3%). mp 205~206° C. $^1$HNMR (CDCl$_3$) δ: 2.34 (6H, 2 s, 2×COCH$_3$), 2.60~2.75 (3H, m, CH$_2$), 3.11~3.16 (2H, m, CH$_2$), 3.28~3.42 (2H, m, CH$_2$), 3.53~3.57 (1H, m, CH$_2$ and N—CH), 3.80 (3H, s, Ar—OCH$_3$), 3.82 (3H, s, Ar—OCH$_3$), 3.99 (1H, d, CH$_2$), 6.70 (1H, s, ArH), 6.90 (1H, s, ArH), 6.97 (1H, s, ArH). MS (EI) m/z: 445 (M$^+$), 444 (M−1), 386 (base), 184, 176, 77.

Example 9

2-benzyloxy-3,10-dimethoxy-9-cinnamoyloxy-12-chloro-5,8,13,13a-tetrahydro-6H-dibenzo[a,g]quinolizine Compound IIA (0.3 g, 0.66 mmol) was dissolved in CH$_2$Cl$_2$ (20 ml), adding cinnamyl chloride (0.132 g, 0.79 mmol) and triethylamine (0.11 ml). The desired product was obtained following the synthetic procedure described in Example 3. The crude solid was recrystallized with CH$_2$Cl$_2$/hexane to give beige product (0.206 g, 53.3%). mp 198~200° C. $^1$HNMR (CDCl$_3$) δ: 2.86~3.01 (3H, m, CH$_2$), 3.41~3.57 (3H, m, CH$_2$ and N—CH), 3.73~3.79 (2H, m, CH$_2$), 4.14 (3H, s, Ar—OCH$_3$), 4.21 (3H, s, Ar—OCH$_3$), 4.35 (1H, d, CH$_2$), 5.50 (2H, q, PhCH$_2$), 6.96 (1H, s, ArH), 7.01 (1H, s, ArH), 7.12 (1H, s, ArH), 7.59 (1H, s, ArH), 7.63~7.82 (8H, m, PhH), 7.92~7.95 (2H, m, PhH), 8.23 (1H, d, CH=R).

Example 10

2-hydroxy-3,10-dimethoxy-9-(3-phenyl-propionyloxy)-12-chloro-5,8,13,13a-tetrahydro-6H-dibenzo[a,g]quinolizine A product obtained in Example 9 (0.06 g, 0.10 mmol) suspend on CH$_3$OH (10 ml), adding Raney-Ni. The mixture was hydrogenated at room temperature for 4 hours. The mixture was filtered, and the filtrate was evaporated under reduced pressure. The residue was purified by silica chromatography (ethyl acetate/petroleum ether=1/4) to give white powder (0.034 g, 51.8%). $^1$HNMR (CDCl$_3$) δ: 2.47~2.68 (3H, m, CH$_2$), 2.92~3.12 (6H, m, CH$_2$), 3.19~3.24 (1H, m, CH$_2$), 3.29~3.36 (1H, dd, CH$_2$), 3.46~3.51 (1H, dd, CH$_2$ and N—CH), 3.76 (3H, s, Ar—OCH$_3$), 3.78 (1H, d, CH$_2$), 3.88 (3H, s, Ar—OCH$_3$), 5.51 (1H, s, Ar—OH), 6.59 (1H, s, ArH), 6.86 (1H, s, ArH), 6.88 (1H, s, ArH), 7.21~7.35 (5H, m, PhH).

Example 11

2,9-dicinnamoyloxy-3,10-dimethoxy-12-chloro-5,8,13,13a-tetrahydro-6H-dibenzo[a,g]quinolizine A product obtained in Example 1 (0.2 g, 0.55 mmol) suspend on CH$_2$Cl$_2$ (20 ml), adding cinnamyl chloride (0.28 g, 1.68 mmol) and triethylamine (0.24 ml). The mixture was stirred at room temperature for 7 hours. Then the mixture was poured into water, adjusting to pH 8 with saturated NaHCO$_3$. The aqueous phase was extracted with CH$_2$Cl$_2$. The combined organic layers were washed with brine and dried over Na$_2$SO$_4$, filtered, and the solvent was evaporated under reduced pressure. The residue was purified by silica chromatography and recrystallized with ethyl acetate/petroleum ether to give pale yellow powder (0.057 g, 16.6%). mp 240~242° C. $^1$HNMR (DMSO-d$_6$) δ: 2.44~2.56 (1H, m, CH$_2$), 2.73~2.78 (1H, m, CH$_2$), 3.01~3.16 (2H, m, CH$_2$), 3.41 (3H, s, CH$_2$), 3.54 (1H, dd, N—CH), 3.78 (3H, s, Ar—OCH$_3$), 3.80 (3H, s, Ar—OCH$_3$), 4.03 (1H, d, CH$_2$), 6.84 (1H, d, CH=R), 6.87 (1H, s, ArH), 6.87 (1H, d, CH=R), 7.13 (1H, s, ArH), 7.15 (1H, s, ArH), 7.46~7.49 (6H, m, PhH), 7.76~7.83 (4H, m, PhH), 7.85 (1H, d, CH=R), 7.89 (1H, d, CH=R).

Example 12

2-benzyloxy-3,10-dimethoxy-9-propyloxy-12-chloro-5,8,13,13a-tetrahydro-6H-dibenzo[a,g]quinolizine Compound IIA (0.3 g, 0.66 mmol) was dissolved in ethanol, adding 1 mol/L NaOH (5 ml) and propyl bromide (1 ml). The mixture was heating to 50~60° C. When the reaction was finished, the mixture was concentrated to small volume followed by adding water. The aqueous phase was extracted with ethyl acetate. The combined organic layers were washed with brine and dried over Na$_2$SO$_4$, filtered, and the solvent was evaporated under reduced pressure. The residue was purified by silica chromatography (ethyl acetate/petroleum ether=1/5) to give desired product (0.10 g, 30.5%). mp 118~120° C. $^1$HNMR (CDCl$_3$) δ: 1.03 (3H, t, CH$_3$), 1.79 (2H, q, CH$_2$), 2.66~2.71 (3H, m, CH$_2$), 3.16~3.21 (3H, m, CH$_2$), 3.46~3.50 (2H, m, CH$_2$ and N—CH), 3.82 (3H, s, Ar—OCH$_3$), 3.89 (3H, s, Ar—OCH$_3$), 3.93~3.97 (2H, t, OCH$_2$), 4.22 (1H, d, CH$_2$), 5.17 (2H, q, PhCH$_2$), 6.64 (1H, s, ArH), 6.79 (1H, s, ArH), 6.84 (1H, s, ArH), 7.26~7.32 (1H, m, PhH), 7.36~7.39 (2H, t, PhH), 7.46~7.48 (2H, d, PhH).

Example 13

2-hydroxy-3,10-dimethoxy-9-propyloxy-12-chloro-5,8,13,13a-tetrahydro-6H-dibenzo[a,g]quinolizine A product obtained in Example 12 (0.045 g, 0.09 mmol) was hydrogenated in the present of Raney-Ni. The desired product was obtained following the synthetic procedure described in Example 1, 4, 7 or 10. The crude product was purified by silica chromatography to give the product (0.026 g, 70.7%). $^1$HNMR (CDCl$_3$) δ: 1.03 (3H, t, CH$_3$), 1.79 (2H, q, CH$_2$), 2.64~2.71 (3H, m, CH$_2$), 3.19~3.53 (5H, m, CH$_2$ and N—CH), 3.82 (3H, s, Ar—OCH$_3$), 3.88 (3H, s, Ar—OCH$_3$), 3.93~3.97 (2H, t, OCH$_2$), 4.24 (1H, d, CH$_2$), 5.54 (1H, brs, Ar—OH), 6.60 (1H, s, ArH), 6.85 (1H, s, ArH), 6.88 (1H, s, ArH).

Example 14

2-benzyloxy-3,10-dimethoxy-9-methanesulfonyloxy-12-chloro-5,8,13,13a-tetrahydro-6H-dibenzo[a,g]quinolizine Compound IIA (0.2 g, 0.44 mmol) was dissolved in pyridine (10 ml), adding methanosulfonyl chloride (0.17 ml) with ice bath and stirring overnight. The mixture was concentrated to small volume under reduced pressure. The residual solution was add CH$_2$Cl$_2$, following filtration. The filtrate was washed with water, saturated NaHCO$_3$ and brine. The solvent was dried over Na$_2$SO$_4$, filtered, and evaporated under reduced pressure. The residue was purified by silica chromatography (ethyl acetate/petroleum ether=1/3) to give desired product (0.086 g, 36.7%). The analytic sample was recrystallized by ethyl acetate/petroleum ether. $^1$HNMR (CDCl$_3$) δ: 2.46~2.69 (3H, m, CH$_2$), 3.02~3.20 (3H, m, CH$_2$), 3.33 (3H, s, SO$_2$CH$_3$), 3.49~3.54 (1H, dd, CH$_2$ and N—CH), 3.62 (1H, d, CH$_2$), 3.87 (3H, s, Ar—OCH$_3$), 3.88 (3H, s, Ar—OCH$_3$), 4.23 (1H, d, CH$_2$), 5.16 (2H, q, PhCH$_2$), 6.63 (1H, s, ArH), 6.75 (1H, s, ArH), 6.92 (1H, s, ArH), 7.29~7.39 (3H, m, PhH), 7.45~7.47 (2H, m, PhH).

Example 15

2-hydroxy-3,10-dimethoxy-9-methanesulfonyloxy-12-chloro-5,8,13,13a-tetrahydro-6H-dibenzo[a,g]quinolizine A product obtained in Example 14 (0.035 g, 0.07 mmol) was hydrogenated in the present of Raney-Ni. The desired product as pale yellow powder (0.027 g, 92.9%) was obtained following the synthetic procedure described in Example 1, 4 or 7. $^1$HNMR (CDCl$_3$) δ: 2.58~2.70 (3H, m, CH$_2$), 3.04~3.24, 3.38~3.39 (3H, m, CH$_2$), 3.34 (3H, s, SO$_2$CH$_3$), 3.54~3.66 (2H, m, CH$_2$ and N—CH), 3.87 (3H, s, Ar—OCH$_3$), 3.88 (3H, s, Ar—OCH$_3$), 4.25 (1H, d, CH$_2$), 5.52 (1H, brs, Ar—OH), 6.60 (1H, s, ArH), 6.87 (1H, s, ArH), 6.93 (1H, s, ArH). MS (EI) m/z: 439 (M$^+$), 360 (base), 344, 183, 176, 77.

Example 16

2-benzyloxy-3,10-dimethoxy-9-(2-hydroxy-ethoxy)-12-chloro-5,8,13,13a-tetrahydro-6H-dibenzo[a,g]quinolizine Compound IIA (0.2 g, 044 mmol), 1-chloroethanol (0.16 ml), K$_2$CO$_3$ (0.38 g, 2.8 mmol), DMF (10 ml) was mixed and heat to 100° C. for 6 hours. The mixture was concentrated to remove DMF and poured into water. The aqueous phase was extracted with ethyl acetate. The combined organic layers were washed with brine and dried over Na$_2$SO$_4$, filtered, and the solvent was evaporated under reduced pressure. The residue was purified by silica chromatography (ethyl acetate/petroleum ether/methanol) and recrystallized with ethyl acetate to give pale yellow crystal (0.157 g, 71.5%). mp 154° C. $^1$HNMR (CDCl$_3$) δ: 2.47~2.70 (3H, m, CH$_2$), 2.82 (1H, brs, OH), 3.11~3.21 (3H, m, CH$_2$), 3.44~3.50 (2H, m, CH$_2$ and N—CH), 3.84 (3H, s, Ar—OCH$_3$), 3.88 (3H, s, Ar—OCH$_3$), 3.84~3.88 (2H, br, OCH$_2$), 3.97~4.01 (1H, m, OCH$_2$), 4.11~4.16 (1H, m, OCH$_2$), 4.22 (1H, d, CH$_2$), 5.16 (2H, q, PhCH$_2$), 6.63 (1H, s, ArH), 6.78 (1H, s, ArH), 6.86 (1H, s, ArH), 7.28~7.32 (1H, m, PhH), 7.35~7.39 (2H, m, PhH), 7.45~7.48 (2H, m, PhH).

Example 17

2-hydroxy-3,10-dimethoxy-9-(2-hydroxy-ethoxy)-12-chloro-5,8,13,13a-tetrahydro-6H-dibenzo[a,g]quinolizine A product obtained in Example 16 (0.08 g, 0.16 mmol) was hydrogenated in the present of Raney-Ni. The desired product was obtained following the synthetic procedure described in Example 1, 4 or 7. The crude product was purified by silica chromatography (ethyl acetate/petroleum ether) to give pale yellow powder (0.013 g, 19.9%). mp 184° C. $^1$HNMR (DMSO-d$_6$) δ: 2.28~2.56 (3H, m, CH$_2$), 2.71~2.88 (2H, m, CH$_2$), 3.04~3.31 (3H, m, CH$_2$ and N—CH), 3.61 (2H, t, OCH$_2$), 3.73 (3H, s, Ar—OCH$_3$), 3.78 (3H, s, Ar—OCH$_3$), 3.94 (2H, m, OCH$_2$), 4.18 (1H, d, CH$_2$), 6.64 (1H, s, ArH), 6.72 (1H, s, ArH), 7.03 (1H, s, ArH).

Example 18

2-benzyloxy-3,10-dimethoxy-9-[2-(2-hydroxy-ethoxy)-ethoxy]-12-chloro-5,8,13,13a-tetrahydro-6H-dibenzo[a,g]quinolizine Compound IIA (0.5 g, 1.1 mmol), 1-chloroethylglycol (0.45 g, 3.6 mmol), K$_2$CO$_3$ (0.31 g, 2.2 mmol), DMF (15 ml) was mixed and heat to 100° C. for 20 hours. After filtering K$_2$CO$_3$, the mixture was concentrated to remove DMF, followed by pouring into water. The aqueous phase was extracted with ethyl acetate. The combined organic layers were washed with brine and dried over Na$_2$SO$_4$, filtered, and the solvent was evaporated under reduced pressure. The residue was purified by silica chromatography (ethyl acetate/petroleum ether) to give yellow needle (0.416 g, 69.6%). The analytic sample was recrystallized with ethyl acetate/petroleum ether. mp 122° C. $^1$HNMR (CDCl$_3$) δ: 2.44~2.69 (3H, m, CH$_2$), 3.07~3.23 (3H, m, CH$_2$), 3.37~3.51 (3H, m, CH$_2$ and N—CH), 3.60~3.71 (5H, m, CH$_2$) 3.82 (3H, s, Ar—OCH$_3$), 3.87 (3H, s, Ar—OCH$_3$), 4.20~4.24 (2H, m, OCH$_2$), 4.39 (1H, d, CH$_2$), 5.16 (2H, q, PhCH$_2$), 6.62 (1H, s, ArH), 6.77 (1H, s, ArH), 6.83 (1H, s, ArH), 7.29~7.31 (1H, m, PhH), 7.34~7.39 (2H, m, PhH), 7.45~7.47 (2H, m, PhH). MS (EI) m/z: 539 (M−1), 448, 283, 91 (base).

Example 19

2-hydroxy-3,10-dimethoxy-9-[2-(2-hydroxy-ethoxy)-ethoxy]-12-chloro-5,8,13,13a-tetrahydro-6H-dibenzo[a,g]quinolizine A product obtained in Example 18 (0.116 g, 0.21 mmol) was hydrogenated in the present of Raney-Ni. The desired product was obtained following the synthetic procedure described in Example 1, 4 or 7. The crude product was purified by silica chromatography (ethyl acetate/petroleum ether/methanol) to give yellow solid (0.035 g, 36.2%). $^1$HNMR (CDCl$_3$) δ: 2.61~2.68 (3H, m, CH$_2$), 3.18~3.70 (1H, m, CH$_2$ and N—CH), 3.81 (3H, s, Ar—OCH$_3$), 3.84 (3H, s, Ar—OCH$_3$), 4.21 (2H, m, OCH$_2$), 4.40 (1H, d, CH$_2$), 6.57 (1H, s, ArH), 6.83 (1H, s, ArH), 6.85 (1H, s, ArH).

Example 20

2-benzyloxy-3,10-dimethoxy-9-ethoxycarbonyloxy-12-chloro-5,8,13,13a-tetrahydro-6H-dibenzo[a,g]quinolizine Compound IIA (0.5 g, 1.1 mmol), ClCOOC$_2$H$_5$ (2.2 mmol), K$_2$CO$_3$ (0.46 g, 3.3 mmol), DMF (10 ml) was mixed and heat to 80° C. When the reaction finished, the mixture was concentrated to remove DMF. The residue was poured into water and extracted with ethyl acetate. The combined organic layers were washed with brine and dried over Na$_2$SO$_4$, filtered, and the solvent was evaporated under reduced pressure. The residue was purified by silica chromatography (ethyl acetate/petroleum ether) to give pale yellow powder (0.195 g, 33.6%). mp 128° C. $^1$HNMR (CDCl$_3$) δ: 1.39 (3H, t, CH$_3$), 2.50~2.68 (3H, m, CH$_2$), 3.12~3.19 (3H, m, CH$_2$), 3.43~3.50 (2H, m, CH$_2$ and N—CH), 3.82 (3H, s, Ar—OCH$_3$), 3.88 (3H, s, Ar—OCH$_3$), 4.07 (1H, d, CH$_2$), 4.32 (2H, q, CH$_2$), 5.16 (2H, q, PhCH$_2$), 6.63 (1H, s, ArH), 6.76 (1H, s, ArH), 6.90 (1H, s, ArH), 7.28~7.32 (1H, m, PhH), 7.35~7.39 (2H, m, PhH), 7.45~7.48 (2H, m, PhH).

Example 21

2-hydroxy-3,10-dimethoxy-9-ethoxycarbonyloxy-12-chloro-5,8,13,13a-tetrahydro-6H-dibenzo[a,g]quinolizine

A product obtained in Example 20 (0.09 g, 0.17 mmol) was hydrogenated in the present of Raney-Ni. The desired product was obtained following the synthetic procedure described in Example 1, 4 or 7. The crude product was recrystallized with $CH_2Cl_2$/hexane to give pink solid (0.044 g, 59.0%). mp 169~170° C. $^1$HNMR ($CDCl_3$) δ: 1.39 (3H, t, $CH_3$), 2.59~2.68 (3H, m, $CH_2$), 3.10~3.16 (2H, m, $CH_2$), 3.33~3.56 (3H, m, $CH_2$ and N—CH), 3.82 (3H, s, Ar—$OCH_3$), 3.88 (3H, s, Ar—$OCH_3$), 4.08 (1H, d, $CH_2$), 4.32 (2H, q, $CH_2$), 5.52 (1H, brs, Ar—OH), 6.60 (1H, s, ArH), 6.87 (1H, s, ArH), 6.91 (1H, s, ArH). MS (EI) m/z: 432 (M−1), 344 (base), 183, 176, 91.

Example 22

2-benzyloxy-3,10-dimethoxy-9-(N-t-Boc-phenylalanyloxy)-12-chloro-5,8,13,13a-tetrahydro-6H-dibenzo[a,g]quinolizine

Method A:

Compound IIA (0.5 g, 1.1 mmol) was dissolved in $CH_2Cl_2$ (20 ml), adding t-Boc-phenylanine (0.88 g, 3.3 mmol) and DCC (0.91 g, 4.4 mmol). The mixture was stirred at room temperature for 6 hours, then cooled in refrigeratory. After filtered, the filtrate was washed with cool citrate buffer, cool saturated $NaHCO_3$ and cool water. The organic layer was dried over $Na_2SO_4$, filtered, and the solvent was evaporated under reduced pressure. The crude product was purified by silica chromatography to give pale yellow solid (0.722 g, 93.3%). mp 140-141° C. $^1$HNMR ($CDCl_3$) δ: 1.41 (9H, 2×s, 3×$CH_3$), 2.46-2.68 (3H, m, $CH_2$), 3.03~3.19 (4H, m, $CH_2$), 3.28~3.49 (3H, m, $CH_2$ and N—CH), 3.79 (3H, d, Ar—$OCH_3$), 3.88 (3H, s, Ar—$OCH_3$), 4.85 (1H, m, $CH_2$), 4.98 (1H, m, COCH), 5.17 (2H, q, Ph$CH_2$), 6.63 (1H, s, ArH), 6.76 (1H, s, ArH), 6.90 (1H, s, ArH), 7.28~7.40 (8H, m, PhH), 7.46~7.48 (2H, m, PhH). MS (EI) m/z: 698 (M$^+$), 641, 450, 434 (base), 360, 91.

Method B:

t-Boc-phenylanine (0.177 g, 0.67 mmol) and CDI (0.227 g, 1.4 mmol) was dissolved in dry THF (10 ml) and stirred at room temperature for 30 minutes. Then the solution of compound IIA (0.3 g, 0.66 mmol) in THF (10 ml) was added and stirred for one day. The mixture was evaporated under reduced pressure and purified by $Al_2O_3$ chromatography to give beige solid (0.114 g, 24.6%).

Example 23

2-benzyloxy-3,10-dimethoxy-9-phenylalanyloxy-12-chloro-5,8,13,13a-tetrahydro-6H-dibenzo[a,g]quinolizine

A product obtained in Example 22 (0.209 g, 0.30 mmol) was stirred with 10% $CF_3COOH$ in $CH_2Cl_2$ at room temperature for 2 hours. Then the mixture was concentrated and added water, adjusting to pH 8 with saturated $NaHCO_3$. The aqueous phase was extracted with $CH_2Cl_2$. The combined organic layers were washed with brine and dried over $Na_2SO_4$, filtered, and the solvent was evaporated under reduced pressure. The residue was purified by silica chromatography to give desired product (0.026 g, 14.5%). $^1$HNMR ($CDCl_3$) δ: 2.46~2.69 (3H, m, $CH_2$), 2.96~3.49 (7H, m, $CH_2$ and N—CH), 3.79 (3H, d, Ar—$OCH_3$), 3.85 (1H, s, $CH_2$), 3.88 (3H, s, Ar—$OCH_3$), 4.03~4.08 (1H, m, COCH), 5.17 (2H, q, Ph$CH_2$), 6.64 (1H, s, ArH), 6.77 (1H, s, ArH), 6.91 (1H, s, ArH), 7.28~7.48 (10H, m, PhH).

Example 24

2-hydroxy-3,10-dimethoxy-9-(N-t-Boc-phenylalanyloxy)-12-chloro-5,8,13,13a-tetrahydro-6H-dibenzo[a,g]quinolizine

A product obtained in Example 22 (0.166 g, 0.24 mmol) was hydrogenated in the present of Raney-Ni. The desired product was obtained following the synthetic procedure described in Example 1, 4 or 7 to give pink powder (0.063 g, 43.6%0. mp 110° C. $^1$HNMR ($CDCl_3$) δ: 1.41 (9H, 2×s, 3×$CH_3$), 2.52~2.68 (3H, m, $CH_2$), 3.02~3.19 (3H, m, $CH_2$), 3.30~3.33 (3H, m, $CH_2$), 3.49~3.53 (1H, m, $CH_2$ and N—CH), 3.79 (3H, d, Ar—$OCH_3$), 3.88 (3H, s, Ar—$OCH_3$), 4.86 (1H, m, $CH_2$), 4.98 (1H, m, COCH), 6.59 (1H, s, ArH), 6.87 (1H, s, ArH), 6.90 (1H, s, ArH), 7.27~7.37 (5H, m, PhH).

Example 25

2-hydroxy-3,10-dimethoxy-9-phenylalanyloxy-12-chloro-5,8,13,13a-tetrahydro-6H-dibenzo[a,g]quinolizine

A product obtained in Example 24 was treat with 10% $CF_3COOH$ in $CH_2Cl_2$. The desired product was obtained following the synthetic procedure described in Example 23.

Example 26

2-benzyloxy-3,10-dimethoxy-9-(N-t-Boc-glycyloxy)-12-chloro-5,8,13,13a-tetrahydro-6H-dibenzo[a,g]quinolizine

Method A:

Compound IIA (0.25 g, 0.55 mmol) was dissolved in $CH_2Cl_2$ (20 ml), adding t-Boc-glycine (0.214 g, 1.22 mmol) and DCC (0.407 g, 1.98 mmol). The mixture was stirred at room temperature for 24 hours, then cooled in refrigeratory. After filtered, the filtrate was washed with cool citrate buffer, cool saturated $NaHCO_3$ and cool water. The organic layer was dried over $Na_2SO_4$, filtered, and the solvent was evaporated under reduced pressure. The crude product was dissolved with ethyl acetate and filtered. The filtrate was recrystallized with ethyl acetate to give pale yellow solid (0.238 g, 70.8%). mp 160° C. $^1$HNMR ($CDCl_3$) δ: 1.46 (9H, s, 3×$CH_3$), 2.49~2.69 (3H, m, $CH_2$), 3.04~3.20 (3H, m, $CH_2$), 3.35~3.50 (2H, m, $CH_2$ and N—CH), 3.79 (3H, s, Ar—$OCH_3$), 3.88 (3H, s, Ar—$OCH_3$), 3.97 (1H, d, $CH_2$), 4.21 (2H, d, $COCH_2$), 5.08 (1H, brs, NH), 5.16 (1H, q, Ph$CH_2$), 6.63 (1H, s, ArH), 6.76 (1H, s, ArH), 6.89 (1H, s, ArH), 7.29~7.32 (1H, m, PhH), 7.35~7.39 (2H, m, PhH), 7.45~7.48 (2H, m, PhH).

Method B:

t-Boc-glycine (0.236 g, 1.35 mmol) was) was dissolved in dry $CH_2Cl_2$ (10 ml), adding CDI (0.32 g, 1.98 mmol). The mixtured was stirred at room temperature for 1 hours and added the solution of compound IIA (0.25 g, 0.55 mmol) in $CH_2Cl_2$ (10 ml). The mixture was stirred for 24 hours, followed evaporating under reduced pressure and purifying by $Al_2O_3$ chromatography to give desired product.

Method C:

t-Boc-glycine (0.29 g, 1.66 mmol), EDCI (0.44 g, 2.2 mmol) and HOBt (0.3 g, 2.2 mmol) was dissolved in THF (10 ml) and stirred at room temperature for 30 minutes. After adding the solution of compound IIA (0.5 g, 1.1 mmol) in THF (10 ml), the mixture was stirred at room temperature for 24 hours. Then the mixture was evaporated under reduced pressure and dissolved in $CH_2Cl_2$. The solution was washed with saturated $NH_4Cl$, saturated $NaHCO_3$ and brine, then dried over $Na_2SO_4$, filtered, and the solvent was evaporated under reduced pressure to give foam solid (0.476 g, 70.8%).

Example 27

2-benzyloxy-3,10-dimethoxy-9-glycyloxy-12-chloro-5,8,13,13a-tetrahydro-6H-dibenzo[a,g]quinolizine Method A:

A product obtained in Example 26 (0.1 g, 0.16 mmol) was treat with 10% $CF_3COOH$ in $CH_2Cl_2$. The mixture was evaporated under reduced pressure to give desired product.

Method B:

A product obtained in Example 26 (0.1 g, 0.16 mmol) was dissolved $CH_2Cl_2$, followed by treating with p-methylphenylsulfonic acid (0.055 g). The mixture was stirred at room temperature, followed by pouring into water. The aqueous phase was adjust to pH 8 with saturated $NaHCO_3$ and extracted with $CH_2Cl_2$. The combined organic layers were washed with brine and dried over $Na_2SO_4$, filtered, and the solvent was evaporated under reduced pressure to give desired product.

Example 28

2-hydroxy-3,10-dimethoxy-9-(N-t-Boc-glycyloxy)-12-chloro-5,8,13,13a-tetrahydro-6H-dibenzo[a,g]quinolizine A product obtained in Example 26 (0.1 g, 0.16 mmol) was hydrogenated in the present of Raney-Ni. The desired product was obtained following the synthetic procedure described in Example 1, 4 or 7. The crude product was purified by silica chromatography (ethyl acetate/petroleum ether) to give yellow powder (0.021 g, 24.6%). mp 213-214° C. $^1$HNMR ($CDCl_3+CD_3OD$) δ: 1.41 (9H, s, 3×$CH_3$), 2.48~2.66 (3H, m, $CH_2$), 2.97~3.18 (2H, m, $CH_2$), 3.34~3.47 (3H, m, $CH_2$ and N—CH), 3.74 (3H, s, Ar—$OCH_3$), 3.78 (3H, s, Ar—$OCH_3$), 3.99 (1H, d, $CH_2$), 4.04 (2H, s, $COCH_2$), 5.08 (1H, brs, NH), 6.59 (1H, s, ArH), 6.73 (1H, s, ArH), 6.97 (1H, s, ArH), 7.69 (1H, s, Ar—OH).

Example 29

2-hydroxy-3,10-dimethoxy-9-glycyloxy-12-chloro-5,8,13,13a-tetrahydro-6H-dibenzo[a,g]quinolizine A product obtained in Example 28 was treat with 10% $CF_3COOH$ in $CH_2Cl_2$. The desired product was obtained following the synthetic procedure described in Example 23.

Example 30

2,9-bis-(N-t-Boc-valyloxy)-3,10-dimethoxy-12-chloro-5,8,13,13a-tetrahydro-6H-dibenzo[a,g]quinolizine A product obtained in Example 1 (0.1 g, 0.28 mmol), t-Boc-valine (0.32 g, 1.47 mmol), DCC (0.23 g, 1.1 mmol), DMAP (0.034 g, 0.28 mmol) and $CH_2Cl_2$ (10 ml) was mixed and stirred at room temperature for 24 hours. The mixture was then cooled in refrigeratory. After filtered, the filtrate was washed with cool citrate buffer, cool saturated $NaHCO_3$ and brine. The organic layer was dried over $Na_2SO_4$, filtered, and the solvent was evaporated under reduced pressure. The crude product was purified by silica chromatography (ethyl acetate/ petroleum ether) to give pale yellow solid (0.146 g, 69.5%). mp 108~110° C. $^1$HNMR ($CDCl_3$) δ: 1.04 (6H, d, 2×$CH_3$), 1.10 (6H, q, 2×$CH_3$), 1.47 (18H, d, 6×$CH_3$), 2.33~2.43 (2H, m, $CH_2$), 2.61~2.74 (3H, m, $CH_2$), 3.13~3.17 (2H, m, $CH_2$ and CH), 3.28~3.56 (3H, m, $CH_2$ and N—CH), 3.77 (3H, s, Ar—$OCH_3$), 3.79 (3H, s, Ar—$OCH_3$), 4.03 (1H, d, $CH_2$), 4.52 (2H, m, COCH), 6.69 (1H, s, ArH), 6.89 (1H, s, ArH), 6.98 (1H, d, ArH).

Example 31

2,9-divalyloxy-3,10-dimethoxy-12-chloro-5,8,13,13a-tetrahydro-6H-dibenzo[a,g]quinolizine A product obtained in Example 30 (0.1 g, 0.13 mmol) was treat with 10% $CF_3COOH$ in $CH_2Cl_2$. The desired product was obtained following the synthetic procedure described in Example 23.

Example 32

(−)-2,10-bis-(N-t-Boc-valyloxy)-3,9-dimethoxy-5,8,13,13a-tetrahydro-6H-dibenzo[a,g]quinolizine l-SPD (0.09 g, 0.27 mmol), t-Boc-valine (0.144 g, 0.66 mmol), DCC (0.189 g, 0.92 mmol), DMAP (0.049 g, 0.4 mmol) and $CH_2Cl_2$ (10 ml) was mixed and stirred at room temperature for 48 hours. The mixture was then cooled in refrigeratory. After filtered, the filtrate was washed with cool citrate buffer, cool saturated $NaHCO_3$ and brine. The organic layer was dried over $Na_2SO_4$, filtered, and the solvent was evaporated under reduced pressure. The crude product was purified by silica chromatography (ethyl acetate/petroleum ether) to give pale yellow solid (0.115 g, 57.6%). $^1$HNMR ($CDCl_3$) δ: 1.02~1.03 (6H, d, 2×$CH_3$), 1.08~1.11 (6H, q, 2×$CH_3$), 1.46~1.48 (18H, d, 6×$CH_3$), 2.36~2.42 (2H, m, $CH_2$), 2.63~2.75 (2H, m, $CH_2$), 2.83~2.89 (1H, m, $CH_2$), 3.14~3.24 (3H, m, $CH_2$ and CH), 3.53~3.57 (2H, m, $CH_2$ and N—CH), 3.78 (3H, s, Ar—$OCH_3$), 3.79 (3H, s, Ar—$OCH_3$), 4.18 (1H, d, $CH_2$), 4.52 (1H, d, COCH), 4.54 (1H, d, COCH), 6.70 (1H, s, ArH), 6.91 (3H, m, ArH).

Example 33

(−)-2,10-divalyloxy-3,9-dimethoxy-5,8,13,13a-tetrahydro-6H-dibenzo[a,g]quinolizine A product obtained in Example 32 (0.1 g, 0.14 mmol) was treat with 10% $CF_3COOH$ in $CH_2Cl_2$. The desired product was obtained following the synthetic procedure described in Example 23.

Example 34

2,9-diacetoxy-3,10-dimethoxy-5,8,13,13a-tetrahydro-6H-dibenzo[a,g]quinolizine A product obtained in Example 2 (0.1 g, 0.27 ml) was dissolved in pyridine (10 ml), adding acetyl anhydride (0.5 ml). The mixture was stirred at room temperature for 2 hours.

The mixture was concentrated under reduced pressure and added water. Then the aqueous phase was adjust to pH 8 with saturated NaHCO$_3$ and extracted with CH$_2$Cl$_2$. The combined organic layers were washed with brine and dried over Na$_2$SO$_4$, filtered, and the solvent was evaporated under reduced pressure to give pale desired product (0.073 g, 64.6%). mp 212~214° C. $^1$HNMR (CDCl$_3$) δ: 2.33 (3H, s, COCH$_3$), 2.34 (3H, s, COCH$_3$), 2.63~2.75 (3H, m, CH$_2$), 3.13~3.20 (3H, m, CH$_2$), 3.41~3.56 (2H, m, CH$_2$ and N—CH), 3.81 (3H, s, Ar—OCH$_3$), 3.82 (3H, s, Ar—OCH$_3$), 4.02 (1H, d, CH$_2$), 6.70 (1H, s, ArH), 6.83 (1H, d, ArH), 6.92 (1H, s, ArH), 7.00 (1H, s, ArH).

Example 35

2-benzyloxy-3,10-dimethoxy-9-{2-[2-(2-hydroxy-ethoxy)-ethoxy]-ethoxy}-12-chloro-5,8,13,13a-tetrahydro-6H-dibenzo[a,g]quinolizine Compound IIA (0.5 g, 1.1 mmol), Cl(CH$_2$CH$_2$O)$_3$H (0.61 g, 3.6 mmol), K$_2$CO$_3$ (0.31 g, 2.2 mmol) and DMF (15 ml) was mixed and heat to 100° C. for 20 hours. After filtering K$_2$CO$_3$, the mixture was concentrated to remove DMF, followed by pouring into water. The aqueous phase was extracted with ethyl acetate. The combined organic layers were washed with brine and dried over Na$_2$SO$_4$, filtered, and the solvent was evaporated under reduced pressure. The residue was purified by silica chromatography (ethyl acetate/petroleum ether) to give yellow powder (0.418 g, 65.1%). The analytic sample was recrystallized with ethyl acetate/petroleum ether. $^1$HNMR (CDCl$_3$) δ: 2.44~2.68 (3H, m, CH$_2$), 3.10~3.25 (3H, m, CH$_2$), 3.37~3.59 (12H, m, CH$_2$ and N—CH), 3.82 (3H, s, Ar—OCH$_3$), 3.87 (3H, s, Ar—OCH$_3$), 4.20~4.24 (2H, m, OCH$_2$), 4.39 (1H, d, CH$_2$), 5.16 (2H, q, PhCH$_2$), 6.62 (1H, s, ArH), 6.77 (1H, s, ArH), 6.83 (1H, s, ArH), 7.26~7.40 (3H, m, PhH), 7.45~7.47 (2H, m, PhH).

Example 36

2-benzyloxy-3,10-dimethoxy-9-{2-[2-(2-methoxy-ethoxy)-ethoxy]-ethoxy}-12-chloro-5,8,13,13a-tetrahydro-6H-dibenzo[a,g]quinolizine Compound IIA (0.5 g, 1.1 mmol), Cl(CH$_2$CH$_2$O)$_3$CH$_3$ (0.66 g, 3.6 mmol), K$_2$CO$_3$ (0.31 g, 2.2 mmol) and DMF (15 ml) was mixed and heat to 100° C. for 20 hours. After filtering K$_2$CO$_3$, the mixture was concentrated to remove DMF, followed by pouring into water. The aqueous phase was extracted with ethyl acetate. The combined organic layers were washed with brine and dried over Na$_2$SO$_4$, filtered, and the solvent was evaporated under reduced pressure. The residue was purified by silica chromatography (ethyl acetate/petroleum ethereum ether) to give yellow powder (0.43 g, 65.3%). The analytic sample was recrystallized with ethyl acetate/petroleum ether. $^1$HNMR (CDCl$_3$) δ: 2.44~2.69 (3H, m, CH$_2$), 3.07~3.23 (3H, m, CH$_2$), 3.37~3.61 (12H, m, CH$_2$ and N—CH), 3.69 (3H, s, OCH$_3$), 3.82 (3H, s, Ar—OCH$_3$), 3.87 (3H, s, Ar—OCH$_3$), 4.06~4.14 (1H, m, OCH$_2$), 4.17~4.23 (1H, m, OCH$_2$), 4.23~4.31 (1H, d, CH$_2$), 5.16 (2H, q, PhCH$_2$), 6.63 (1H, s, ArH), 6.79 (1H, s, ArH), 6.83 (1H, s, ArH), 7.25~7.41 (3H, m, PhH), 7.45~7.47 (2H, m, PhH).

Example 37

2-benzyloxy-3,10-dimethoxy-9-ethoxyoxalyloxy-12-chloro-5,8,13,13a-tetrahydro-6H-dibenzo[a,g]quinolizine Compound IIA (0.2 g, 0.44 mmol) was dissolved in pyridine (10 ml), adding ClCOCOOC$_2$H$_5$ (0.25 ml, 0.66 mmol) under ice bath. The mixture was stirred at room temperature overnight. Then the mixture was concentrated to small volume and added CH$_2$Cl$_2$. After filtering, the filtrate was washed with water, saturated NaHCO$_3$ and brine. The solution was dried over Na$_2$SO$_4$, filtered, and the solvent was evaporated under reduced pressure. The residue was purified by silica chromatography (ethyl acetate/petroleum ether=1/3) to give desired product (0.11 g, 45.2%). $^1$HNMR (CDCl$_3$) δ: 1.32 (3H, s, CH$_2$CH$_3$) 2.46~2.69 (3H, m, CH$_2$), 3.02~3.20 (3H, m, CH$_2$), 3.49~3.61 (2H, m, CH$_2$ and N—CH), 3.87 (3H, s, Ar—OCH$_3$), 3.88 (3H, s, Ar—OCH$_3$), 4.06~4.14 (2H, m, OCH$_2$), 4.23 (1H, d, CH$_2$), 5.17 (2H, q, PhCH$_2$), 6.65 (1H, s, ArH), 6.74 (1H, s, ArH), 6.91 (1H, s, ArH), 7.29~7.35 (3H, m, PhH), 7.45~7.49 (2H, m, PhH).

Example 38

2,9-diundecanoyloxy-3,10-dimethoxy-12-chloro-5,8,13,13a-tetrahydro-6H-dibenzo[a,g]quinolizine A product obtained in Example 1 (0.2 g, 0.55 mmol) was suspend on CH$_2$Cl$_2$ (20 ml), adding hendecyl chloride (0.50 ml, 1.85 mmol) and triethylamine (0.24 ml). The mixture was stirred at room temperature for 7 hours. Then the mixture was poured into water, adjusting to pH 9 with saturated NaHCO$_3$. The aqueous phase was extracted with CH$_2$Cl$_2$. The combined organic layers were washed with brine and dried over Na$_2$SO$_4$, filtered, and the solvent was evaporated under reduced pressure. The residue was purified by silica chromatography to give yellow oil (0.19 g, 49.3% 0. $^1$HNMR (CDCl$_3$) δ: 0.97 (6H, 2 s, 2CH$_3$), 1.31~1.55 (32H, m, CH$_2$), 2.11~2.23 (4H, m, CH$_2$), 2.61~2.75 (3H, m, CH$_2$), 3.13~3.16 (2H, m, CH$_2$), 3.28~3.41 (2H, m, CH$_2$), 3.55~3.57 (1H, m, CH$_2$ and N—CH), 3.80 (3H, s, Ar—OCH$_3$), 3.81 (3H, s, Ar—OCH$_3$), 3.96 (1H, d, CH$_2$), 6.73 (1H, s, ArH), 6.92 (1H, s, ArH), 6.96 (1H, s, ArH).

Example 39

2-benzyloxy-3,10-dimethoxy-9-undecanoyloxy-12-chloro-5,8,13,13a-tetrahydro-6H-dibenzo[a,g]quinolizine Compound IIA (0.15 g, 0.33 mmol) was dissolved in pyridine (7 ml), adding hendecyl chloride (0.2 ml, 0.75 mmol). The mixture was stirred at room temperature overnight. Then the mixture was concentrated to remove pyridine and the residue added CH$_2$Cl$_2$. After filtering the insoluble solid, the filtrate was washed with water, saturated NaHCO$_3$ and brine. The solution was dried over Na$_2$SO$_4$, filtered, and the solvent was evaporated under reduced pressure. The residue was purified by silica chromatography to give yellow oil (0.16 g, 78.2%). $^1$HNMR (CDCl$_3$) δ: 0.95 (3H, s, CH$_3$), 1.32~1.56 (16H, m, CH$_2$), 2.12~2.21 (2H, m, CH$_2$), 2.46~2.68 (3H, m, CH$_2$), 3.02~3.21 (3H, m, CH$_2$), 3.49~3.62 (2H, m, CH$_2$ and N—CH), 3.89 (3H, s, Ar—OCH$_3$), 3.88 (3H, s, Ar—OCH$_3$), 4.24 (1H, d, CH$_2$), 5.18 (2H, q, PhCH$_2$), 6.66 (1H, s, ArH), 6.74 (1H, s, ArH), 6.92 (1H, s, ArH), 7.29~7.36 (3H, m, PhH), 7.43~7.48 (2H, m, PhH).

Example 40

2-benzyloxy-3,10-dimethoxy-9-(undec-10-enyloxy)-12-chloro-5,8,13,13a-tetrahydro-6H-dibenzo[a,g]quinolizine Compound IIA (0.15 g, 0.33 mmol) was dissolved in pyridine (7 ml), adding undec-10-enoyl chloride (0.2 ml, 0.74 mmol). The mixture was stirred at room temperature overnight. Then the mixture was concentrated to remove pyridine and the residue added $CH_2Cl_2$. After filtering the insoluble solid, the filtrate was washed with water, saturated $NaHCO_3$ and brine. The solution was dried over $Na_2SO_4$, filtered, and the solvent was evaporated under reduced pressure. The residue was purified by silica chromatography to give yellow oil (0.15 g, 73.2%). $^1HNMR$ ($CDCl_3$) δ: 1.32~1.56 (14H, m, $CH_2$), 2.12~2.21 (2H, m, $CH_2$), 2.46~2.68 (3H, m, $CH_2$), 3.02~3.21 (3H, m, $CH_2$), 3.49~3.62 (2H, m, $CH_2$ and N—CH), 3.89 (3H, s, Ar—$OCH_3$), 3.88 (3H, s, Ar—$OCH_3$), 4.24 (1H, d, $CH_2$), 4.89~5.10 (2H, m, C=$CH_2$), 5.18 (2H, q, $PhCH_2$), 5.32 (1H, m, C=CH) 6.66 (1H, s, ArH), 6.74 (1H, s, ArH), 6.92 (1H, s, ArH), 7.29~7.36 (3H, m, PhH), 7.43~7.48 (2H, m, PhH).

Example 41

2-hydroxy-3,10-dimethoxy-9-undecanoyloxy-12-chloro-5,8,13,13a-tetrahydro-6H-dibenzo[a,g]quinolizine A product obtained in Example 39 (0.07 g, 0.1 mmol) was hydrogenated in the present of Raney-Ni. The desired product was obtained following the synthetic procedure described in Example 1, 4 or 7. The product was given as pale brown oil (0.05 g, 85.8%). $^1HNMR$ ($CDCl_3$) δ: 0.95 (3H, s, $CH_3$), 1.32~1.56 (16H, m, $CH_2$), 2.12~2.21 (2H, m, $CH_2$) 2.58~2.70 (3H, m, $CH_2$), 3.04~3.24, 3.38~3.39 (3H, m, $CH_2$), 3.54~3.66 (2H, m, $CH_2$ and N—CH), 3.87 (3H, s, Ar—$OCH_3$), 3.88 (3H, s, Ar—$OCH_3$), 4.25 (1H, d, $CH_2$), 5.52 (1H, brs, Ar—OH), 6.60 (1H, s, ArH), 6.87 (1H, s, ArH), 6.93 (1H, s, ArH).

Example 42

2,9-bis-{2-[2-(2-methoxy-ethoxy)-ethoxy]-acetoxy-}3,10-dimethoxy-12-chloro-5,8,13,13a-tetrahydro-6H-dibenzo[a,g]quinolizine A product obtained in Example 1 (0.22 g, 0.61 mmol) suspend on $CH_2Cl_2$ (22 ml), adding $CH_3(OCH_2CH_2)_2OCH_2COCl$ (0.25 ml, 1.81 mmol) and triethylamine (0.24 ml). The mixture was stirred at room temperature for 15 hours. Then the mixture was poured into water and extracted with $CH_2Cl_2$. The combined organic layers were washed with saturated $NaHCO_3$ and brine. The solution was dried over $Na_2SO_4$, filtered, and the solvent was evaporated under reduced pressure. The residue was purified by silica chromatography to give yellow oil (0.19 g, 45.3%). $^1HNMR$ ($CDCl_3$) δ: 2.61~2.75 (3H, m, $CH_2$), 3.13~3.26 (3H, m, $CH_2$), 3.28~3.41 (6H, m, $CH_3$), 3.51~3.75 (18H, m, $CH_2$ and N—CH), 3.80 (3H, s, Ar—$OCH_3$), 3.81 (3H, s, Ar—$OCH_3$), 3.96 (1H, d, $CH_2$), 4.16~4.35 (4H, m, $OCH_2$) 6.73 (1H, s, ArH), 6.92 (1H, s, ArH), 6.96 (1H, s, ArH).

Example 43

2-hydroxy-3,10-dimethoxy-9-{2-[2-(2-methoxy-ethoxy)-ethoxy]-acetoxy-}-12-chloro-5,8,13,13a-tetrahydro-6H-dibenzo[a,g]quinolizine Compound IIA (0.2 g, 0.44 mmol) was dissolved in pyridine (10 ml), adding $CH_3(OCH_2CH_2)_2OCH_2COCl$ (0.2 ml, 0.72 mmol). The mixture was stirred at room temperature overnight. Then the mixture was concentrated to remove pyridine and the residue was added $CH_2Cl_2$. After filtering the insoluble solid, the filtrate was washed with water, saturated $NaHCO_3$ and brine. The solution was dried over $Na_2SO_4$, filtered, and the solvent was evaporated under reduced pressure. The residue was purified by silica chromatography to give 2-hydroxy-3,10-dimethoxy-9-{2-[2-(2-methoxy-ethoxy)-ethoxy]-acetoxy}-12-chloro-5,8,13,13a-tetrahydro-6H-dibenzo[a,g]quinolizine. The compound is yellow oil (0.23 g, 84.2%). $^1HNMR$ ($CDCl_3$) δ: 2.61~2.75 (3H, m, $CH_2$), 3.13~3.26 (3H, m, $CH_2$), 3.28~3.41 (3H, m, $CH_3$), 3.51~3.75 (10H, m, $CH_2$ and N—CH), 3.80 (3H, s, Ar—$OCH_3$), 3.81 (3H, s, Ar—$OCH_3$), 3.96 (1H, d, $CH_2$), 4.16~4.35 (2H, m, $OCH_2$), 5.18 (2H, q, $PhCH_2$), 6.73 (1H, s, ArH), 6.92 (1H, s, ArH), 6.96 (1H, s, ArH), 7.29~7.36 (3H, m, PhH), 7.43~7.48 (2H, m, PhH).

The product obtained above was hydrogenated in the present of Raney-Ni. The desired product was obtained following the synthetic procedure described in Example 1, 4 or 7.

Example 44

2,3,9,10-tetrahydroxy-12-chloro-5,8,13,13a-tetrahydro-6H-dibenzo[a,g]quinolizine A product obtained in Example 1 (0.3 g, 0.66 mmol) was dissolved in $CH_2Cl_2$ (20 ml), adding a solution of $BBr_3$ (0.32 ml) in $CH_2Cl_2$ (5 ml) under ice-salt bath. The mixture was stirred for 1 hours at this temperature, then stirred at room temperature overnight. The reactant solution produced yellow precipitate. The mixture was poured into water and stirred for 30 minute. After filtering, the solid was dissolved with methanol. Then the mixture was filtered. The filtrate was evaporated under reduced pressure, followed by recrystallizing with methanol to give yellow solid (0.15 g, 67.7%). mp 295~296° C. $^1HNMR$ (DMSO-$d_6$) δ: 2.65~2.86 (3H, m, $CH_2$), 3.05~3.63 (5H, m, $CH_2$ or N—CH), 4.29 (1H, d, $CH_2$), 6.59 (1H, s, ArH), 6.81 (1H, s, ArH), 6.92 (1H, s, ArH). MS (EI) m/z: 333 ($M^+$), 299, 164 (base), 107, 80.

Example 45

2-hydroxy-3,10-dimethoxy-9-(2-hydroxy-ethoxy)-12-chloro-N-methyl-5,8,13,13a-tetrahydro-6H-dibenzo[a,g]quinolizine A product obtained in Example 17 (0.1 g) was dissolved in THF (20 ml), adding iodomethane (0.1 ml). The mixture was stirred at room temperature overnight. The yellow solid precipitating was filtered and dried to give yellow powder.

Example 46

(−)-2-hydroxy-3,10-dimethoxy-9-valyloxy-12-chloro-5,8,13,13a-tetrahydro-6H-dibenzo[a,g]quinolizine Compound (−)-IIA (preparation as the method reported in CN03151464.2) was treat with N-CBz-L-valine. According the procedure described in method C of Example 26, compound (−)-2-benzyloxy-9-O-(t-Boc-valine)acyl-3,10-dimethoxy-12-chloro-5,8,13,13a-tetrahydro-6H-dibenzo[a,g]quinolizine was obtained. This compound was debenzyl with Pd—C/$H_2$ (the method described in Example 2). Then the crude product was purified by silica chromatography to give desired product.

Example 47

(−)-2,9-diacetoxy-3,10-dimethoxy-12-chloro-5,8,13,13a-tetrahydro-6H-dibenzo[a,g]quinolizine Compound (−)-IIA was hydrogenated in the present of Raney-Ni according the procedure described in Example 1 to give (−)-2,9-dihydroxy-3,10-dimethoxy-12-chloro-5,8,13,13a-tetrahydro-6H-dibenzo[a,g]quinolizine. This compound was acetylation with acetyl anhydride according the method described in Example 6 to give desired product. The total yield is 81%. mp 202~203° C. Anal: Cacl: C, 61.95%; H, 5.43%; N, 3.14%; test: C, 62.18%; H, 5.35%; N, 3.06%. $[\alpha]^{25}_D = -254°(C=0.2, CHCl_3)$. $^1HNMR$ ($CDCl_3$) δ: 2.34 (6H, 2 s, 2×$COCH_3$), 2.58~2.76 (3H, m, $CH_2$), 3.11~3.17 (2H, m, $CH_2$), 3.28~3.43 (2H, m, $CH_2$), 3.55 (1H, dd, N—CH), 3.80 (3H, s, Ar—$OCH_3$), 3.82 (3H, s, Ar—$OCH_3$), 3.99 (1H, d, $CH_2$), 6.71 (1H, s, ArH), 6.91 (1H, s, ArH), 6.97 (1H, s, ArH). MS (EI) m/z: 445 ($M^+$), 444 (M−1), 386 (base), 184, 176, 77.

Example 48

(−)-2,10-diacetoxy-3,9-dimethoxy-5,8,13,13a-tetrahydro-6H-dibenzo[a,g]quinolizine l-SPD (0.264 g, 0.81 mmol), pyridine (1 ml) and acetyl anhydride (0.5 ml) was mixtured and stirred at room temperature for 0.5 hours. The mixture was poured into water, then yellow solid was precipitated. The solid was collected by filtering and wash with water, then dried at 40° C. to give pale yellow solid (0.235 g, 70.8%). Anal: cacl: C, 67.14%; H, 6.12%; N, 3.40%; test: C, 67.46%; H, 5.97%; N, 3.30%. $^1HNMR$ ($CDCl_3$) δ:2.32 (6H, 2 s, 2×$COCH_3$), 2.61~2.91 (3H, m, $CH_2$), 3.14~3.29 (3H, m, $CH_2$), 3.51~3.60 (2H, m, $CH_2$ and N—CH), 3.81 (3H, s, Ar—$OCH_3$), 3.82 (3H, s, Ar—$OCH_3$), 4.20 (1H, d, J=15.9 Hz, $CH_2$), 6.71 (1H, s, ArH), 6.90 (2H, s, ArH), 6.92 (1H, s, ArH). MS (EI) m/z: 411 ($M^+$), 368, 220, 176, 150 (base), 135.

Example 49

(−)-2-benzyloxy-3,10-dimethoxy-9-acetoxy-12-chloro-5,8,13,13a-tetrahydro-6H-dibenzo[a,g]quinolizine Starting from compound (−)-IIA, the desired product was obtained following the synthetic procedure described in Example 6 to give white powder. It can be used in next step without purification.

Example 50

(−)-2-hydroxy-3,10-dimethoxy-9-acetoxy-12-chloro-5,8,13,13a-tetrahydro-6H-dibenzo[a,g]quinolizine Starting from the product obtained in Example 49, the desired product was obtained following the synthetic procedure described in Example 7 to give pink powder. The total yield from compound IIA was 63.26%. mp 172~173° C. Anal: calcd: C, 62.45%; H, 5.49%; N, 3.47%; test: C, 62.31%; H, 5.33%; N, 3.28%. $[\alpha]^{25}_D = -235°$ ($CHCl_3$). MS (EI) m/z: 405 (M+2), 403 ($M^+$), 360, 344 (base), 186, 149, 91.

Example 51

(−)-2,9-bis-(N-benzyloxycarbonyl-valyloxy)-3,10-dimethoxy-12-chloro-5,8,13,13a-tetrahydro-6H-dibenzo[a,g]quinolizine Compound (−)-IIA was hydrogenated in the present of Raney-Ni according the procedure described in Example 1 to give (−)-2,9-dihydroxy-3,10-dimethoxy-12-chloro-5,8,13,13a-tetrahydro-6H-dibenzo[a,g]quinolizine.

The methanesulfonate of this compound (0.6 g, 1.3 mmol), N-CBz-valine (1.32 g, 5.26 mmol), DCC (1.08 g, 5.24 mmol) and DMAP (0.16 g, 1.31 mmol) was mixed with $CH_2Cl_2$ (20 ml) and stirred at room temperature for 6 hours. Then the mixture was cooled in refrigeratory. After filtered, the filtrate was evaporated under reduced pressure. The crude product was purified by silica chromatography (ethyl acetate/petroleum ether) to give pale yellow solid (1.01 g, 93.1%). The analytic sample was recrystallized with ethyl acetate/petroleum ether. $^1HNMR$ ($CDCl_3$) δ: 1.04 (6H, d, 2×$CH_3$), 1.11 (6H, d, 2×$CH_3$), 2.40~2.47 (2H, m, $CH_2$), 2.60~2.74 (3H, m, $CH_2$), 3.09~3.15 (2H, m, $CH_2$ and CH), 3.29~3.57 (3H, m, $CH_2$ and N—CH), 3.76 (3H, s, Ar—$OCH_3$), 3.78 (3H, s, Ar—$OCH_3$), 3.98 (1H, d, J=12 Hz, $CH_2$), 4.62 (2H, m, COCH), 5.16 (4H, s, $OCH_2Ph$), 5.34 (1H, d, NH), 5.39 (1H, d, NH), 6.69 (1H, s, ArH), 6.89 (1H, s, ArH), 6.95 (1H, d, ArH), 7.32~7.40 (10H, m, PhH).

Example 52

(−)-2-benzyloxy-3,10-dimethoxy-9-ethoxycarbonylmethoxy-12-chloro-5,8,13,13a-tetrahydro-6H-dibenzo[a,g]quinolizine Compound (−)-IIA (1.0 g, 2.2 mmol) was dissolved in dry DMF (10 ml), adding $BrCH_2COOC_2H_5$ (0.27 ml, 2.4 mmol), $K_2CO_3$ (0.61 g, 4.4 mmol). The mixture was stirred at room temperature for 6 hours. After filtering $K_2CO_3$, the filtrate was concentrated to remove DMF, followed by adding water. The aqueous phase was extracted two times with $CH_2Cl_2$. The combined organic layers were washed with brine and dried over $Na_2SO_4$, filtered, and the solvent was evaporated under reduced pressure. The residue was dissolved with ethyl acetate and filtered. The filtrate was recrystallized with ethyl acetate/petroleum ether to give white powder (0.4 g, 34%).

Example 53

2-benzyloxy-3,10-dimethoxy-9-ethoxycarbonylmethoxy-12-chloro-5,8,13,13a-tetrahydro-6H-dibenzo[a,g]quinolizine The desired product was obtained following the synthetic procedure described in Example 52. The crude product was purified by silica chromatography to give milk white powder. mp 134° C. $^1HNMR$ ($CDCl_3$) δ:1.31 (3H, t, $CH_3$), 2.46~2.70 (3H, m, $CH_2$), 3.10~3.21 (3H, m, $CH_2$), 3.46 (1H, dd, N—$CH_2$), 3.53 (1H, d, $CH_2$), 3.81 (1H, s, Ar—$OCH_3$), 3.88 (1H, s, Ar—$OCH_3$), 4.26 (2H, q, $OCH_2CH_3$), 4.35 (1H, d, $CH_2$), 4.63 (2H, q, $OCH_2CO$), 5.16 (2H, q, $PhCH_2O$), 6.64 (1H, s, ArH), 6.78 (1H, s, ArH), 6.84 (1H, s, ArH), 7.27~7.40 (3H, m, PhH), 7.45~7.48 (2H, m, PhH).

Example 54

(−)-2-hydroxy-3,10-dimethoxy-9-ethoxycarbonylmethoxy-12-chloro-5,8,13,13a-tetrahydro-6H-dibenzo[a,g]quinolizine Starting from the product obtained in Example 52, the desired product was obtained following the synthetic procedure described in Example 1 to give pale yellow powder. The analytic sample was recrystallized with ethyl acetate/petroleum ether. mp 202~204° C. $^1$HNMR (CD$_3$OD) δ:1.26 (3H, t, CH$_3$), 2.84~3.11 (2H, m, CH$_2$), 3.22~3.34 (4H, m, CH$_2$), 3.55 (1H, td, N—CH), 3.71~3.82 (1H, d, CH$_2$), 3.86 (1H, s, Ar—OCH$_3$), 3.88 (1H, s, Ar—OCH$_3$), 4.20 (2H, q, OCH$_2$CH$_3$), 4.50 (1H, d, CH$_2$), 4.76 (2H, q, OCH$_2$CO), 5.07 (2H, q, PhCH$_2$), 6.83 (1H, s, ArH), 6.85 (1H, s, ArH), 7.21 (1H, s, ArH).

Example 55

2-hydroxy-3,10-dimethoxy-9-ethoxycarbonyl-methoxy-12-chloro-5,8,13,13a-tetrahydro-6H-dibenzo[a,g]quinolizine Starting from the product obtained in Example 53, the desired product was obtained following the synthetic procedure described in Example 54 to give milk white powder. mp 132° C.

Example 56

(−)-2-hydroxy-3,10-dimethoxy-9-carboxymethoxy-12-chloro-5,8,13,13a-tetrahydro-6H-dibenzo[a,g] quinolizine A product obtained in Example 54 (1.92 g, 4.3 mmol) was dissolved in ethanol (20 ml), adding NaOH (0.343 g, 8.6 mmol, dissolved in 10 ml water). The mixture was stirred at room temperature for 2 hours. Then the mixture was concentrated under reduced pressure followed by adding water. The aqueous phase was washed with ethyl acetate and adjust to pH 3~4 by 1 mol/L hydrochloric acid. The precipitated solid was collected by filtration and washed by water. Recrystallizing with methanol/water to give yellow powder (1.11 g, 62%). mp 179~180° C. $[α]^{25}_D$=−149° (CH$_3$OH). $^1$HNMR (DMSO-d$_6$) δ:2.40~2.50 (2H, m, CH$_2$), 2.65~2.76 (2H, m, CH$_2$), 2.91~2.99 (1H, m, CH$_2$), 3.30~3.56 (3H, m, CH$_2$ and N—CH), 3.74 (1H, s, Ar—OCH$_3$), 3.80 (1H, s, Ar—OCH$_3$), 4.41 (1H, d, CH$_2$), 4.63 (2H, q, OCH$_2$CO), 6.69 (1H, s, ArH), 6.76 (1H, s, ArH), 7.12 (1H, s, ArH).

Example 57

2-hydroxy-3,10-dimethoxy-9-carboxymethoxy-12-chloro-5,8,13,13a-tetrahydro-6H-dibenzo[a,g]quinolizine A product obtained in Example 55 (3.1 g, 6.9 mmol) was dissolved in ethanol (50 ml), adding 1 mol/L NaOH (13.9 ml). The mixture was stirred at room temperature for 2 hours. Then the mixture was concentrated under reduced pressure followed by adding water. The aqueous phase was washed with ethyl acetate and adjust to pH 5~6 by 1 mol/L hydrochloric acid. The precipitated solid was collected by filtration and washed by water to give pale yellow powder. The solid was dissolved in alkali solution and adjust the pH again to give the refine product (2.6 g, 89.5%). mp 172~174° C. $^1$HNMR (DMSO-d$_6$) δ: 2.30~2.49 (2H, m, CH$_2$), 2.58~2.63 (1H, d, CH$_2$), 2.89~2.95 (1H, m, CH$_2$), 3.08 (1H, dd, CH$_2$), 3.23 (1H, dd, N—CH), 3.38~3.47 (2H, m, CH$_2$), 3.74 (3H, s, Ar—OCH$_3$), 3.79 (1H, s, Ar—OCH$_3$), 4.25 (1H, d, CH$_2$), 4.59 (2H, q, OCH$_2$CO), 6.66 (1H, s, ArH), 6.73 (1H, s, ArH), 7.05 (1H, s, ArH).

Example 58

2-benzyloxy-3,10-dimethoxy-9-carboxymethoxy-12-chloro-5,8,13,13a-tetrahydro-6H-dibenzo[a,g]quinolizine Starting from the product obtained in Example 53 (0.32 g, 0.59 mmol), the desired product was obtained following the synthetic procedure described in Example 57 to give pale yellow powder (0.22 g, 73.7%). $^1$HNMR (DMSO-d$_6$) δ: 2.30 (1H, dd, CH$_2$), 2.58~2.69 (2H, m, CH$_2$), 2.89~2.95 (1H, m, CH$_2$), 3.14 (1H, d, CH$_2$), 3.32 (1H, dd, N—CH), 3.39~3.49 (2H, m, CH$_2$), 3.74 (3H, s, Ar—OCH$_3$), 3.79 (1H, s, Ar—OCH$_3$), 4.30 (1H, d, CH$_2$), 4.61 (2H, q, OCH$_2$CO), 5.07 (2H, s, OCH$_2$Ph), 6.73 (1H, s, ArH), 6.98 (1H, s, ArH), 7.07 (1H, s, ArH), 7.29~7.48 (5H, s, PhH).

Starting from the product descried above (Example 58), the product in Example 57 was also obtained following the synthetic procedure described in Example 55.

Example 59

(−)-2,9-diethoxycarbonylmethoxy-3,10-dimethoxy-12-chloro-5,8,13,13a-tetrahydro-6H-dibenzo[a,g] quinolizine Compound (−)-IIA was hydrogenated in the present of Raney-Ni according to the procedure described in Example 1 to give (−)-2,9-dihydroxy-3,10-dimethoxy-12-chloro-5,8,13,13a-tetrahydro-6H-dibenzo[a,g]quinolizine.

The compound described above (3.3 g, 9.1 mmol) was dissolved in dry DMF (10 ml), adding BrCH$_2$COOC$_2$H$_5$ (2.53 ml) and K$_2$CO$_3$ (3.78 g). The mixture was stirred at room temperature for 2 hours. After filtering K$_2$CO$_3$, the filtrate was concentrated to remove DMF, followed by diluting with water. The aqueous phase was extracted two times with CH$_2$Cl$_2$. The combined organic layers were washed with brine and dried over Na$_2$SO$_4$, filtered, and the solvent was evaporated under reduced pressure. The residue was purified by silica chromatography (ethyl acetate/petroleum ether) to give compounds 59a, 59b and 59c.

59a: (−)-2,9-diethoxycarbonylmethoxy-3,10-dimethoxy-12-chloro-5,8,13,13a-tetrahydro-6H-dibenzo[a,g]quinolizine Crude compound 59a was recrystallized with ethyl acetate/petroleum ether to give desired white powder (1.3 g, 26.7%). $^1$HNMR (CD$_3$Cl) δ: 1.31 (6H, t, CH$_3$×2), 2.55~2.71 (3H, m, CH$_2$), 3.08~3.32 (3H, m, CH$_2$), 3.48~3.57 (2H, m, CH$_2$ and N—CH), 3.81 (3H, s, Ar—OCH$_3$), 3.87 (3H, s, Ar—OCH$_3$), 4.22~4.33 (4H, m, OCH$_2$CH$_3$×2), 4.37 (1H, d, CH$_2$), 4.55~4.75 (4H, q, $\overline{\text{OCH}_2\text{CO}}$×2), 6.64 (1H, s, ArH), 6.79 (1H, s, ArH), 6.84 (1H, s, ArH).

59b: (−)-2,9-diethoxycarbonylmethoxy-3,10-dimethoxy-12-chloro-N-α-ethoxycarbonylmethyl-5,8,13,13a-tetrahydro-6H-dibenzo[a,g]quinolizine Compound 59b (0.15 g, 2.3%) was yellow powder. $^1$HNMR (CD$_3$Cl) δ: 1.28 (9H, m, CH$_3$×3), 2.84 (1H, m, CH$_2$), 3.17~3.25 (2H, m, CH$_2$), 3.42~3.64 (2H, m, CH$_2$), 3.84 (3H, s, Ar—OCH$_3$), 3.89 (3H, s, Ar—OCH$_3$), 4.16~4.31 (6H, m, O CH$_2$CH$_3$×3), 4.59 (1H, m, CH$_2$), 4.65 (2H, m, OCH$_2$CO), $\overline{4.71}$ (2H, s, NCH$_2$CO), 4.95 (1H, d, CH$_2$ or N—CH), 5.44

(1H, d, CH$_2$), 5.68 (2H, q, OCH$_2$CO), 6.13 (1H, m, CH$_2$), 6.74 (1H, s, ArH), 6.82 (1H, s, ArH), 6.95 (1H, s, ArH).

59c: (−)-2,9-diethoxycarbonylmethoxy-3,10-dimethoxy-12-chloro-N-β-ethoxycarbonylmethyl-5,8,13,13a-tetrahydro-6H-dibenzo[a,g]quinolizine Compound 59c (0.2 g, 3.1%) was yellow powder. $^1$HNMR (CD$_3$Cl) δ: 1.28 (9H, m, CH$_3$×3), 2.68~2.78 (1H, m, CH$_2$), 3.01 (1H, m, CH$_2$), 3.26 (1H, m, CH$_2$), 3.72 (2H, m, CH$_2$), 3.85 (3H, s, Ar—OCH$_3$), 3.89 (3H, s, Ar—OCH$_3$), 4.11~4.33 (6H, m, OCH$_2$CH$_3$×3), 4.62 (2H, m, OCH$_2$CO), 4.72 (1H, m, CH$_2$), 4.81 (2H, s, NCH$_2$CO), 4.98 (1H, d, OCH$_2$CO), 5.22 (1H, d, CH$_2$ or N—CH), 5.64 (1H, d, OCH$_2$CO), 5.93 (1H, d, CH$_2$), 6.49 (1H, m, CH$_2$), 6.73 (1H, s, ArH), 6.83 (1H, s, ArH), 7.00 (1H, s, ArH).

Example 60

2,9-diethoxycarbonylmethoxy-3,10-dimethoxy-12-chloro-5,8,13,13a-tetrahydro-6H-dibenzo[a,g]quinolizine The desired product was obtained following the synthetic procedure described in Example 59.

Example 61

(−)-2,9-dicarboxymethoxy-3,10-dimethoxy-12-chloro-5,8,13,13a-tetrahydro-6H-dibenzo[a,g]quinolizine Starting from the product obtained in Example 59a (1.33 g, 2.49 mmol), the desired product was obtained following the synthetic procedure described in Example 56 to give yellow powder (0.653 g, 54.9%). mp 230~232° C. $^1$HNMR (DMSO-d$_6$) δ:2.24~2.33 (1H, m, CH$_2$), 2.60~2.64 (1H, d, CH$_2$), 2.86~2.95 (1H, m, CH$_2$), 3.05 (1H, dd, CH$_2$), 3.26 (1H, dd, N—CH), 3.36~3.42 (3H, m, CH$_2$), 3.74 (3H, s, Ar—OCH$_3$), 3.76 (1H, s, Ar—OCH$_3$), 4.25 (1H, d, CH$_2$), 4.51 (4H, s, OCH$_2$CO), 6.71 (1H, s, ArH), 6.81 (1H, s, ArH), 7.01 (1H, s, ArH). MS (EI) m/z: 478 (M$^+$), 476 (M−2), 418 (base), 344, 183, 91, 77.

Example 62

2,9-dicarboxymethoxy-3,10-dimethoxy-12-chloro-5,8,13,13a-tetrahydro-6H-dibenzo[a,g]quinolizine Staring from the product obtained in Example 60, the desired product was obtained following the synthetic procedure described in Example 61 to give yellow powder. Yield: 90%. mp 202~204° C. $^1$HNMR (DMSO-d$_6$) δ: 2.25~2.34 (1H, m, CH$_2$), 2.60~2.65 (1H, d, CH$_2$), 2.86~2.90 (1H, m, CH$_2$), 3.05 (1H, dd, CH$_2$), 3.27 (1H, dd, N—CH), 3.37~3.44 (3H, m, CH$_2$), 3.77 (3H, s, Ar—OCH$_3$), 3.78 (1H, s, Ar—OCH$_3$), 4.25 (1H, d, CH$_2$), 4.52 (4H, s, OCH$_2$CO), 6.71 (1H, s, ArH), 6.81 (1H, s, ArH), 7.02 (1H, s, ArH).

Example 63

2,3-methylenedioxyl-9,10-dimethoxy-12-fluoro-5,8,13,13a-tetrahydro-6H-dibenzo[a,g]quinolizine 2,3-methylenedioxyl-9,10-dimethoxy-12-amino-5,8,13,13a-tetrahydro-6H-dibenzo[a,g]quinolizine (0.1 g, 0.28 mmol) was suspend on HBF$_4$ (5 mL), cooling to −10° C. in ice-salt bath. A solution of NaNO$_2$ (0.19 g) in water (1.5 mL) was dropped slowly to control the temperature <−8° C. When finished, the mixture was stirred in ice bath for 0.5~1 hours, followed cooling in refrigeratory. The precipitate was collected by filtering and washed by cool water and cool ethanol to give pale yellow powder (0.12 g). The powder was pyrolyzed in 110° C. The crude product was purified by silica chromatography (CH$_2$Cl$_2$/methanol) to give pale yellow powder (0.05 g, 49.6%). $^1$H NMR (CDCl$_3$) δ: 2.57~2.69 (3H, m, CH$_2$), 3.13~3.22 (2H, m, CH$_2$), 3.31 (1H, dd, CH$_2$), 3.34~3.55 (2H, m, CH$_2$ and N—CH), 3.80 (3H, s, Ar—OCH$_3$), 3.83 (3H, s, Ar—OCH$_3$), 4.23 (1H, d, CH$_2$), 5.92 (2H, s, OCH$_2$O), 6.56 (1H, s, Ar—H), 6.59 (1H, s, Ar—H), 6.76 (1H, s, Ar—H). MS (EI) m/z: 357 (M$^+$), 326, 182, 167 (base), 149. MS (HR-EI) m/z: 357.1380 (M$^+$); calcd: 357.1376.

The invention claimed is:

1. A compound of the formula (I), their stereoisomers, or pharmacologically acceptable salts:

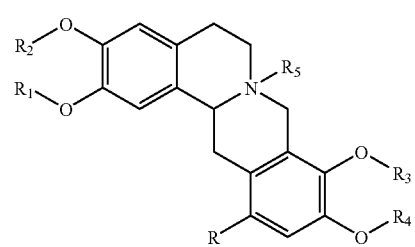

wherein

R is H or halogen;

when R is halogen,

R$_1$ is selected from H, (CH$_2$CH$_2$O)$_n$R$_6$ (n=1~3), amino acid radical, COR$_7$, or R$_1$ and R$_2$ together form (CH$_2$)$_n$ and n is 1 or 2;

each of R$_3$ and R$_4$ is selected from H, C$_1$~C$_{12}$ alkyl, (CH$_2$CH$_2$O)$_n$R$_6$ (n=1~3), amino acid radical, COR$_7$;

when R$_3$ or R$_4$ is C$_1$~C$_{12}$ alkyl, the alkyl is saturated or unsaturated alkyl, linear chain C$_1$~C$_{12}$ alkyl, branched chain C$_1$~C$_{12}$ alkyl, C$_3$~C$_{12}$ cycloalkyl, C$_1$~C$_{12}$ alkyl substituted by aryl or COOR$_6$; when R$_1$, R$_3$ or R$_4$ is an amino acid radical, the amino acid is D-, L- or DL-amino acid;

R$_6$ is selected from H, C$_1$~C$_3$ alkyl or alkyl substituted by aryl;

R$_7$ is selected from C$_1$~C$_{12}$ alkyl, alkoxy, COR$_8$, (CH$_2$)$_n$NR$_9$R$_{10}$, substituted aryl, unsubstituted aryl, heterocyclic radical selected from imidazolyl, pyrazolyl, pyrrolidinyl, pyridinyl; when R$_7$ is C$_1$~C$_{12}$ alkyl, the alkyl is saturated or unsaturated alkyl, linear chain C$_1$~C$_{12}$ alkyl, branched chain C$_1$~C$_{12}$ alkyl, C$_3$~C$_{12}$ cycloalkyl, C$_1$~C$_{12}$ alkyl substituted by phenyl;

R$_8$ is selected from H, alkyl, alkoxy or aryl;

each of R$_9$ and R$_{10}$ is H;

R$_2$ is selected from H, C$_1$~C$_3$ alkyl, or R$_1$ and R$_2$ together form (CH$_2$)$_n$ and n is 1 or 2;

R$_5$ is H, O, C$_1$~C$_3$ alkyl, substituted C$_1$~C$_3$ alkyl, or there is no existing R$_5$;

the said compounds exclude the following known compounds:

2,9-dihydroxy-3,10-dimethoxy-12-chloro-5,8,13,13a-tetrahydro-6H-dibenzo[a,g]quinolizine;

2,10-dihydroxy-3,9-dimethoxy-12-chloro-5,8,13,13a-tetrahydro-6H-dibenzo[a,g]quinolizine;

3,9,10-trimethoxy-2-hydroxy-12-chloro-5,8,13,13a-tetrahydro-6H-dibenzo[a,g]quinolizine;
2,9-dihydroxy-3,10-dimethoxy-12-bromo-5,8,13,13a-tetrahydro-6H-dibenzo[a,g]quinolizine;
2,10-dihydroxy-3,9-dimethoxy-12-bromo-5,8,13,13a-tetrahydro-6H-dibenzo[a,g]quinolizine;
3,9,10-trimethoxy-2-hydroxy-12-bromo-5,8,13,13a-tetrahydro-6H-dibenzo[a,g]quinolizine;
2,9-dihydroxy-3,10-dimethoxy-12-fluoro-5,8,13,13a-tetrahydro-6H-dibenzo[a,g]quinolizine;
2,9-dihydroxy-3,10-dimethoxy-12-iodo-5,8,13,13a-tetrahydro-6H-dibenzo[a,g]quinolizine;
2,3-methylenedioxyl-9-hydroxy-10-methoxy-12-chloro-5,8,13,13a-tetrahydro-6H-dibenzo[a,g]quinolizine;
2,3-methylenedioxyl-9,10-dimethoxy-12-chloro-5,8,13,13a-tetrahydro-6H-dibenzo[a,g]quinolizine;
2,3-methylenedioxyl-9-hydroxy-10-methoxy-12-bromo-5,8,13,13a-tetrahydro-6H-dibenzo[a,g]quinolizine;
2,3-methylenedioxyl-9,10-dimethoxy-12-bromo-5,8,13,13a-tetrahydro-6H-dibenzo[a,g]quinolizine;
when R is H;
$R_1$ is selected from H, $(CH_2CH_2O)_nR_6$ (n=1~3), amino acid radical, $COR_7$, or $R_1$ and $R_2$ together form $(CH_2)_n$, n is 1 or 2;
each of $R_3$ and $R_4$ is selected from H, $C_1$~$C_{12}$ alkyl, $(CH_2CH_2O)_nR_6$ (n=1~3), amino acid radical, $COR_7$; and at least one of $R_3$ and $R_4$ is $COR_7$;
when $R_3$ or $R_4$ is $C_1$~$C_{12}$ alkyl, the alkyl is saturated or unsaturated alkyl, linear chain $C_1$~$C_{12}$ alkyl, branched chain $C_1$~$C_{12}$ alkyl, $C_3$~$C_{12}$ cycloalkyl, $C_1$~$C_{12}$ alkyl substituted by aryl or $COOR_6$; when $R_1$, $R_3$ or $R_4$ is amino acid radical, the amino acid is D-, L- or DL-amino acid;
$R_6$ is selected from H, $C_1$~$C_3$ alkyl or alkyl substituted by aryl;
$R_7$ is selected from $C_1$~$C_{12}$ alkyl, alkoxy, $COR_8$, $(CH_2)_n NR_9R_{10}$, substituted aryl, unsubstituted aryl, heterocyclic radical selected from imidazolyl, pyrazolyl, pyrrolidinyl, pyridinyl; when $R_7$ is $C_1$~$C_{12}$ alkyl, the alkyl is saturated or unsaturated alkyl, linear chain $C_1$~$C_{12}$ alkyl, branched chain $C_1$~$C_{12}$ alkyl, $C_3$~$C_{12}$ cycloalkyl, $C_1$~$C_{12}$ alkyl substituted by phenyl;
$R_8$ is selected from H, alkyl, alkoxy or aryl;
each of $R_9$ and $R_{10}$ is H;
$R_2$ is selected from H, $C_1$~$C_3$ alkyl, or $R_1$ and $R_2$ together form $(CH_2)_n$, n is 1 or 2;
$R_5$ is H, $C_1$~$C_3$ alkyl, substituted $C_1$~$C_3$ alkyl, or there is no existing of $R_5$; when $R_1$ is H, one of $R_3$ and $R_4$ only can be selected from unsubstituted $C_3$~$C_{12}$ alkyl, substituted $C_2$-$C_{12}$ alkyl $(CH_2CH_2O)_nR_6$(n=1~3), amino acid radical, $COR_7$;
when $R_1$=$COCH_3$ and $R_2$=$R_4$=$CH_3$, $R_3$ can't be $CH_3$ or $COCH_3$;
when $R_1$ and $R_2$ together form $CH_2$, $R_3$ and $R_4$ can't be selected from H, $CH_3$, $C_2H_5$, $COCH_3$, 4-methoxy benzoyl radical or 3,4,5-trimethoxy benzoyl radical at the same time;
in the definition mentioned above, halogen is F, Cl, Br or I;
any two of $R_1$, $R_2$, $R_3$, $R_4$ are same or different group mentioned above.

2. The compound according to claim 1, wherein
when R is H,
$R_1$ is H, $COR_7$, amino acid radical, or $R_1$ and $R_2$ together form $CH_2$; $R_7$ is selected from $C_1$~$C_{12}$ alkyl, $COR_8$, alkoxy, or alkyl substituted by $(CH_2CH_2O)_nR_6$ (n=1~3); $R_6$ is H, $C_1$~$C_3$ alkyl or alkyl substituted by aryl; $R_8$ is alkoxy;
$R_2$ is H, methyl, or $R_2$ and $R_1$ together form $CH_2$;
$R_3$ is H, methyl, $COR_7$ or amino acid radical;
$R_4$ is H, methyl, $COR_7$ or amino acid radical;
and at least one of $R_3$ and $R_4$ is $COR_7$;
when R is Cl or F,
$R_1$ is H, $COR_7$, amino acid radical, or $R_1$ and $R_2$ together form $CH_2$; $R_7$ is selected from $C_1$~$C_{12}$ alkyl, $COR_8$, alkoxy, or alkyl substituted by $(CH_2CH_2O)_nR_6$ (n=1~3); $R_6$ is H, $C_1$~$C_3$ alkyl or alkyl substituted by aryl; $R_8$ is alkoxy;
$R_2$ is H, methyl, or $R_2$ and $R_1$ together form $CH_2$;
$R_3$ is H, methyl, $COR_7$ or amino acid radical;
$R_4$ is H, methyl, $COR_7$ or amino acid radical.

3. A compound, their stereoisomers, or pharmacologically acceptable salts selected from:
2-hydroxy-3,10-dimethoxy-9-acetoxy-12-chloro-5,8,13,13a-tetrahydro-6H-dibenzo[a,g]quinolizine;
2,9-diacetoxy-3,10-dimethoxy-12-chloro-5,8,13,13a-tetrahydro-6H-dibenzo[a,g]quinolizine;
2-hydroxy-3,10-dimethoxy-9-(2-hydroxy-ethoxy)-12-chloro-5,8,13,13a-tetrahydro-6H-dibenzo[a,g]quinolizine;
2-hydroxy-3,10-dimethoxy-9-ethoxycarbonyloxy-12-chloro-5,8,13,13a-tetrahydro-6H-dibenzo[a,g]quinolizine;
2-benzyloxy-3,10-dimethoxy-9-phenylalanyloxy-12-chloro-5,8,13,13a-tetrahydro-6H-dibenzo[a,g]quinolizine;
2,9-diacetoxy-3,10-dimethoxy-5,8,13,13a-tetrahydro-6H-dibenzo[a,g]quinolizine;
2,9-bis-{2-[2-(2-methoxy-ethoxy)-ethoxy]-acetoxy}-3,10-dimethoxy-12-chloro-5,8,13,13a-tetrahydro-6H-dibenzo[a,g]quinolizine;
2-hydroxy-3,10-dimethoxy-9-{2-[2-(2-methoxy-ethoxy)-ethoxy]-acetoxy}-12-chloro-5,8,13,13a-tetrahydro-6H-dibenzo[a,g]quinolizine;
2,3,9,10-tetrahydroxy-12-chloro-5,8,13,13a-tetrahydro-6H-dibenzo[a,g]quinolizine;
(−)-2,9-diacetoxy-3,10-dimethoxy-12-chloro-5,8,13,13a-tetrahydro-6H-dibenzo[a,g]quinolizine;
(−)-2,10-diacetoxy-3,9-dimethoxy-5,8,13,13a-tetrahydro-6H-dibenzo[a,g]quinolizine;
(−)-2-hydroxy-3,10-dimethoxy-9-acetoxy-[2-chloro-5,8,13,13a-tetrahydro-6H-dibenzo[a, g]quinolizine; and
2,3-methylenedioxyl-9,10-dimethoxy-12-fluoro-5,8,13,13a-tetrahydro-6H-dibenzo[a,g]quinolizine.

4. The compound according to claim 1 or 3, wherein their pharmacologically acceptable salts are salts of the compounds with an acid, including hydrochloric acid, hydrobromic acid, sulfuric acid, phosphoric acid, carboxylic acid, organic sulfonic acid; or salts of the compounds with an alkali, including an alkali metal salt of the compound, including sodium or potassium salt of the compound.

5. A method of preparing the compounds according to claim 1, comprising:
(1) preparing a compound of formula (I):

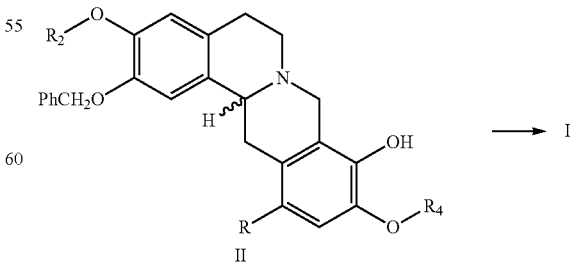

from compound of formula (II) using one of following methods:

1) Compound of formula (II) is reacted with $R_3Cl$ or $R_3Br$; the temperature is in the range of 0° C.-100° C., the reaction is catalysed by inorganic alkali or organic alkali, wherein the inorganic alkali is NaOH, KOH, CsOH, $Ba(OH)_2$, $Mg(OH)_2$, $Ca(OH)$, $KHCO_3$, $K_2CO_3$, $Na_2CO_3$ or $Cs_2CO_3$, the organic alkali is sodium alkoxide, $NEt_3$, $N(C_4H_9)_3$ or $N(C_3H_7)_3$, the mixture was stirred at 0-100° C. for 2-24 hours to give compound of formula (I); the solvent is selected from the group including methanol, ethanol, isopropanol, $C_4H_9OH$, iso-$C_4H_9OH$, t-$C_4H_9OH$, $C_5H_{11}OH$, iso-$C_5H_{11}OH$, and the mixture of the above alcohol and water, in which alcohol: water=0.5:9.5-9.5:0.5(V: V), or from the group including DMF, $CH_2Cl_2$, DMSO, THF, dioxane, pyrrolidone, acetone and $CH_3OCH_2CH_2OCH_3$;

2) Compound of formula (II) is reacted with $R_3COCl$, $(R_3CO)_2O$ or $R_3(CO)_2O$; the reaction carry through in the presence of inorganic alkali or organic alkali at 0-100° C., wherein the inorganic alkali is NaOH, KOH, CsOH, $Ba(OH)_2$, $Mg(OH)_2$, $Ca(OH)_2$, $KHCO_3$, $K_2CO_3$, $Na_2CO_3$ or $Cs_2CO_3$, the organic alkali is pyridine, $NEt_3$, $N(C_4H_9)_3$, $N(C_3H_7)_3$; stirring the mixture at 0-100° C. for 2-8 hours to give a compound of formula (I); the solvent is selected from Pyridine, DMF, $CH_2Cl_2$, DMSO, THF, dioxane and pyrrolidone; and a catalyst DMAP is added according the reaction conditions;

4) a compound of formula (II) is reacted with an N-protected amino acid; the reaction of THPBs with amino acid is finished through one of the procedures: <1> THPBs is esterificated by a acylchlorated N-protected amino acid to give the desired compound; or <2> treat THPBs of formula (II) and N-protected amino acid in the present of amino acid catalyst; the reaction is carried through at 0° C. to room temperature to give a desired compound; the solvent is selected from $CH_2Cl_2$, DMF or THF; and the catalyst is selected in DCC, CDI, EDCI or other coupled reagent, accompanied by HOBt or DMAP;

5) the deprotection of a desired compound prepared by 4) to give formula (I), which is carried through in the presence of inorganic acid or organic acid at 0° C. to room temperature, wherein the inorganic acid is HCl or $H_2SO_4$, the organic acid is toluenesulfonic acid, $CF_3COOH$ or AcOH; and the solvent is selected from $CH_2Cl_2$ or THF;

6) when $R_1$=H, a compound of formula (I) is obtained by hydrogenating the compound of formula (II) ($R_1$=$CH_2Ph$) in the present of catalyst at 0-40° C. for 1-10 h; the catalyst is a Raney-Ni, and the solvent is methanol, ethanol, isopropanol or a mixture solution of the above alcohol and water;

(2) preparation from formula (IV):

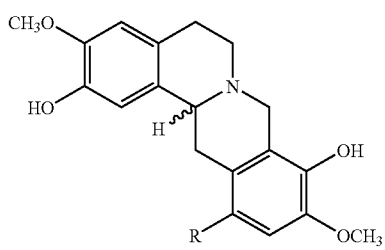

a compound of formula (I) is prepared from the compound of formula (IV) using one of the following methods:
1) the compound of formula (IV) is reacted with $R_1Cl$ or $R_1Br$ in a different ratio of amount to give a compound of formula (I); 2) a compound of formula (IV) is reacted with $R_1COCl$, $(R_1CO)_2O$, $R_3COCl$ or $(R_3CO)_2O$ in a different ratio of amount to give a compound of formula (I);

(3) preparation from formula (V):

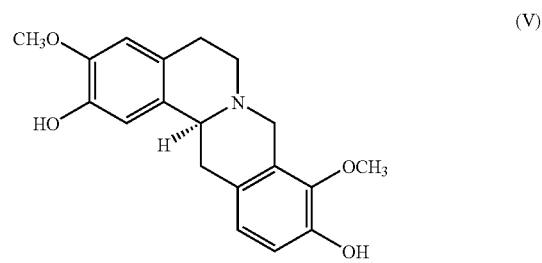

the compound of formula (V) is I-SPD; starting from I-SPD, the compound of formula (I) is provided by esterification, etherification, coupling with an amino acid or demethylation;

(4) preparing a compound of formula (I), wherein, $R_5$ is $C_1$~$C_3$ alkyl or substituted $C_1$~$C_3$ alkyl:
the free base of compound of formula (I) is reacted with alkyl halide or substituted alkyl halide at room temperature to 100° C., followed by precipitating when cooling, or by separating through column chromatography to give the target product;

(5) preparation from formula (VI):

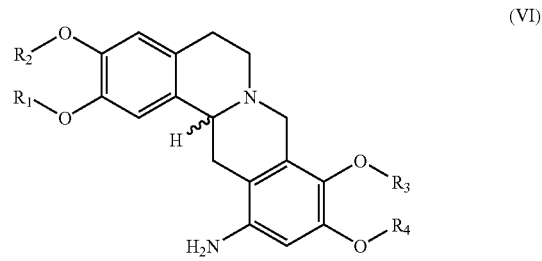

wherein the compound of formula (VI) is treated with $HNO_2$ to give a diazo salt, which is reacted with a corresponding reagent to give the compound of formula (I) (R=halogen), wherein, without specific indication, the definitions for R, $R_1$, $R_2$, $R_3$ and $R_4$ are the same as described in claim 1.

6. The method according to claim 5, wherein a compound of formula (I), wherein R2, R3 or R4 is benzyl, is debenzylated in the presence of Raney-Ni at 0-40° C. for 1-10 hours to give a compound of formula (I); wherein the solvent is alcohol, or a mixture solution of the alcohol and water.

7. The method according to claimed 5, wherein a compound of formula (II) is reacted with an N-protected amino acid in the present of amino acid catalyst at 0° C. to room temperature to give the desired compound; the solvent is selected from $CH_2Cl_2$, DMF or THF; the catalyst is selected from DCC, CDI or EDCI or other coupled reagent, accompanied by HOBt or DMAP.

8. A method of treating a condition of schizophrenia, parkinsonism, hyperactivity disorder or migraine comprising administering to a subject in need thereof an effective amount of a compound of formula I, it's stereoisomers, or pharmacologically acceptable salts:

(I)

wherein
R is H or halogen;
$R_1$ is selected from H, $(CH_2CH_2O)_nR_6$ (n=1~3), amino acid radical, $COR_7$, or $R_1$ and $R_2$ together form $(CH_2)_n$, n is 1 or 2;
each of $R_3$ and $R_4$ is selected from H, $C_1$~$C_{12}$ alkyl, $(CH_2CH_2O)_nR_6$ (n=1~3), amino acid radical, $COR_7$;
when $R_3$ or $R_4$ is $C_1$~$C_{12}$ alkyl, the alkyl is saturated or unsaturated alkyl, linear chain $C_1$~$C_{12}$ alkyl, branched chain $C_1$~$C_{12}$ alkyl, $C_3$~$C_{12}$ cycloalkyl, $C_1$~$C_{12}$ alkyl substituted by aryl or $COOR_6$; when $R_1$, $R_3$ or $R_4$ is amino acid radical, the amino acid is D-, L- or DL-amino acid;
$R_6$ is selected from H, $C_1$~$C_3$ alkyl or alkyl substituted by aryl;
$R_7$ is selected from $C_1$~$C_{12}$ alkyl, alkoxy, $COR_8$, $(CH_2)_n$ $NR_9R_{10}$, substituted aryl, unsubstituted aryl, heterocyclic radical selected from imidazolyl, pyrazolyl, pyrrolidinyl, pyridinyl; when $R_7$ is $C_1$~$C_{12}$ alkyl, the alkyl is saturated or unsaturated alkyl, linear chain $C_1$~$C_{12}$ alkyl, branched chain $C_1$~$C_{12}$ alkyl, $C_3$~$C_{12}$ cycloalkyl, $C_1$~$C_{12}$ alkyl substituted byphenyl;
$R_8$ is selected from H, alkyl, alkoxy or aryl;
each of $R_9$ and $R_{10}$ is H;
$R_2$ is selected from H, $C_1$~$C_3$ alkyl, or $R_1$ and $R_2$ together form $(CH_2)_n$, n is 1 or 2;
$R_5$ is H, O, $C_1$~$C_3$ alkyl, substituted $C_1$~$C_3$ alkyl, or there is no existing of $R_5$;
in the definition mentioned above, halogen is F, Cl, Br or I;
any two of $R_1$, $R_2$, $R_3$, $R_4$ are same or different group mentioned above;
among the above compounds, when R is H, $R_1$~$R_4$ is limited as follow:
when $R_1$ is H, one of $R_3$ and $R_4$ only can be selected from unsubstituted $C_2$~$C_{12}$ alkyl, substituted $C_2$~$C_{12}$ alkyl, $(CH_2CH_2O)_nR_6$(n=1~3), amino acid radical, $COR_7$;
when $R_1$=$COCH_3$ and $R_2$=$R_4$=$CH_3$, $R_3$ can't be $CH_3$ or $COCH_3$;
when $R_1$ and $R_2$ together form $CH_2$, $R_3$ and $R_4$ can't be selected from H, $CH_3$, $C_2H_5$, $COCH_3$, 4-methoxy benzoyl radical or 3,4,5-trimethoxy benzoyl radical at the same time;
and when R=halogen, the said compounds exclude the following known compounds:
2,9-dihydroxy-3,10-dimethoxy-12-chloro-5,8,13,13a-tetrahydro-6H-dibenzo[a,g]quinolizine;
2,10-dihydroxy-3,9-dimethoxy-12-chloro-5,8,13,13a-tetrahydro-6H-dibenzo[a,g]quinolizine;
3,9,10-trimethoxy-2-hydroxy-12-chloro-5,8,13,13a-tetrahydro-6H-dibenzo[a,g]quinolizine;
2,9-dihydroxy-3,10-dimethoxy-12-bromo-5,8,13,13a-tetrahydro-6H-dibenzo[a,g]quinolizine;
2,10-dihydroxy-3,9-dimethoxy-12-bromo-5,8,13,13a-tetrahydro-6H-dibenzo[a,g]quinolizine;
3,9,10-trimethoxy-2-hydroxy-12-bromo-5,8,13,13a-tetrahydro-6H-dibenzo[a,g]quinolizine;
2,9-dihydroxy-3,10-dimethoxy-12-fluoro-5,8,13,13a-tetrahydro-6H-dibenzo[a,g]quinolizine;
2,9-dihydroxy-3,10-dimethoxy-12-iodo-5,8,13,13a-tetrahydro-6H-dibenzo[a,g]quinolizine;
2,3-methylenedioxyl-9-hydroxy-10-methoxy-12-chloro-5,8,13,13a-tetrahydro-6H-dibenzo[a,g]quinolizine;
2,3-methylenedioxyl-9,10-dimethoxy-12-chloro-5,8,13,13a-tetrahydro-6H-dibenzo[a,g]quinolizine;
2,3-methylenedioxyl-9-hydroxy-10-methoxy-12-bromo-5,8,13,13a-tetrahydro-6H-dibenzo[a,g]quinolizine;
2,3-methylenedioxyl-9,10-dimethoxy-12-bromo-5,8,13,13a-tetrahydro-6H-dibenzo[a,g]quinolizine.

* * * * *